(12) United States Patent
Chao et al.

(10) Patent No.: US 6,723,740 B2
(45) Date of Patent: Apr. 20, 2004

(54) ACTIVATOR OF PPAR DELTA

(75) Inventors: Esther Yu-Hsuan Chao, Durham, NC (US); Curt Dale Haffner, Durham, NC (US); Millard Hurst Lambert, III, Durham, NC (US); Patrick Reed Maloney, Durham, NC (US); Michael Lawrence Sierra, Les Ulis, NC (US); Daniel David Sternbach, Durham, NC (US); Marcos Luis Sznaidman, Durham, NC (US); Timothy Mark Willson, Durham, NC (US); Huaqiang Eric Xu, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/383,011

(22) Filed: Mar. 6, 2003

(65) Prior Publication Data
US 2003/0203947 A1 Oct. 30, 2003

Related U.S. Application Data

(63) Continuation of application No. 10/018,935, filed as application No. PCT/EP00/05720 on Jun. 22, 2000.

(30) Foreign Application Priority Data

Jun. 25, 1999 (GB) ............................................. 9914977

(51) Int. Cl.[7] .................... A61K 31/421; A61K 31/426; C07D 277/20; C07D 263/30
(52) U.S. Cl. ...................... 514/365; 514/374; 548/203; 548/235
(58) Field of Search ................ 514/365, 374; 548/203, 235

(56) References Cited

U.S. PATENT DOCUMENTS 5,847,008 A 12/1998 Doebber et al.

FOREIGN PATENT DOCUMENTS

| JP | 53555 | 2/1995 |
|---|---|---|
| JP | 165735 | 6/1995 |
| JP | 104688 | 4/1996 |
| JP | 325250 | 12/1996 |
| JP | 124623 | 5/1997 |
| JP | 194467 | 7/1997 |
| JP | 323982 | 12/1997 |
| WO | WO 9728149 | 8/1997 |
| WO | WO 9807699 | 2/1998 |
| WO | WO 9904815 | 2/1999 |
| WO | WO 9946232 | 8/1999 |

OTHER PUBLICATIONS

Shinkai Hisashi et al., Isoxazolidine–3,5–dione and Non-cyclic 1,3–Dicarbonyl Compounds as Hypoglycemic Agents, *J. Medicinal Chemistry*, 1998, vol. 41, pp. 1927–1933.

S.W. Bright et al., Monoclonal antibodies as surrogate receptors in a high throughput screen for compounds that enhance insulin sensitivity, Life Sciences, vol. 61, No. 23, pp. 2305–2315, 1997.

*Primary Examiner*—Joseph K. McKane
*Assistant Examiner*—Golam M M Shameem
(74) *Attorney, Agent, or Firm*—Robert H. Brink

(57) ABSTRACT

Compounds of Formula (I) are disclosed.

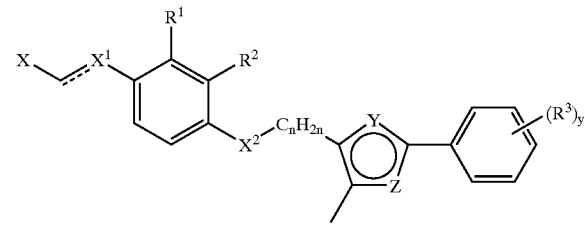

These compounds selected activators of human PPAR delta.

1 Claim, No Drawings

ACTIVATOR OF PPAR DELTA

This application is a continuation of application Ser. No. 10/018,935, filed Dec. 19, 2001 which is a rule 371 U.S. National Phase Application of PCT Application No. PCT/EP00/05720, filed Jun. 22, 2000, which claims priority to GB Application Serial No. 9914977.5, filed Jun. 25, 1999.

The present invention relates to certain novel compounds. In particular, the present invention relates to compounds that activate the delta subtype of the human peroxisome proliferator activated receptor ("hPPARδ"). The present invention also relates to method for preparing and using the novel compounds and to methods for using activators of hPPARδ.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. Curr. Pharm. Des. 1998, 4, 53–70).

Syndrome X (including metabolic syndrome) is loosely defined as a collection of abnormalities including hyperinsulinemia, obesity, elevated levels of trigycerides, uric acid, fibrinogen, small dense LDL particles, and plasminogen activator inhibitor 1 (PAI-1), and decreased levels of HDL-c.

NIDDM (non insulin dependent or Type 2 diabetes mellitus) is described as insulin resistance which in turn causes anomalous glucose output and a decrease in glucose uptake by skeletal muscle. These factors eventually lead to impaired glucose tolerance (IGT) and hyperinsulinemia.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, Trends Endoodn. Met 291–296, 4 (1993)).

It has now been reported that thiazolidinediones are potent and selective activators of PPAR-gamma and bind directly to the PPAR-gamma receptor (J. M. Lehmann et. al., J. Biol. Chem. 12953–12956, 270 (1995)), providing evidence that PPAR-gamma is a possible target for the therapeutic actions of the thiazolidinediones.

Activators of the nuclear receptor PPARγ gamma, for example troglitazone, have been shown in the clinic to enhance insulin-action, reduce serum glucose and have small but significant effects on reducing serum triglyceride levels in patients with Type 2 diabetes. See, for example, D. E. Kelly et al., Curr. Opin. Endocrinol. Diabetes, 90–96, 5 (2), (1998); M. D. Johnson et al., Ann. Pharmacother., 337–348, 32 (3), (1997); and M. Leutenegger et al., Curr. Ther. Res., 403–416, 58 (7), (1997).

The mechanism for this triglyceride lowering effect appears to be predominantly increased clearance of very low density lipoproteins (VLDL) through induction of liporotein lipase (LPL) gene expression. See, for example, B. Staels et al., Artedoscler. Thromb., Vasc. Biol., 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., Curr. Pharm. Des., 1–14, 3 (1), (1997). Activation of PPAR alpha results in transcription of enzymes that increase fatty acid catabolism and decrease de-novo fatty acid synthesis in the liver resulting in decreased triglyceride synthesis and VLDL production/secretion. In addition, PPAR alpha activation decreases production of apoC-III. Reduction in apoC-III, an inhibitor of LPL activity, increases clearance of VLDL. See, for example, J. Auwerx et al., Atherosclerosis, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.). In a recent report (Berger et al., J. Biol. Chem. 1999), vol. 274, pp. 6718–6725) it was stated that PPAR delta activation does not appear to modulate glucose or triglyceride levels.

Briefly, in one aspect, the present invention provides compounds of formula (I), and pharmaceutically acceptable salts and, solvates thereof, wherein

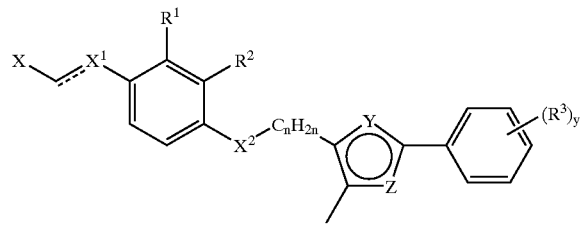

X represents a COOH (or a hydrolysable ester thereof) or tetrazole group;

$X^1$ represents NH, NCH$_3$, O, S, a bond (i.e. is absent), CH$_2$, or CH where the dashed line indicates that when $X^1$ is CH the depicted bond is a double bond;

$X^2$ represents O or S;

$R^1$ and $R^2$ independently represent H, CH$_3$, OCH$_3$, or halogen;

n is 1 or 2;

one of Y and Z is N and the other is S or O:

y is 0, 1, 2, 3, 4 or 5;

Each $R^3$ independently represents CF$_3$ or halogen.

In another aspect, the present invention discloses a method for prevention or treatment of a human PPAR delta ("hPPARδ") mediated disease or condition comprising administration of a therapeutically effective amount of a compound of this invention. hPPARδ mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, Type 2 diabetes mellitus, Type I diabetes, insulin resistance, hyperlipidemia, and regulation of appetite and food intake in subjects suffering from disorders such as obesity, anorexia bulimia, and anorexia nervosa. In particular, the compounds of this invention are useful in the treatment and prevention of cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPARδ mediated disease or condition.

In another aspect, the present invention provides a method for lowering triglycerides by administration of a hPPARδ agonist. Preferably the hPPARδ agonist is a selective agonist.

In another aspect the present invention provides the use of a hPPARδ agonist for the manufacture of a medicament for lowering triglyceride levels. Preferably the hPPARδ agonist is a selective agonist.

In a further aspect the present invention provides a method for treating Type 2 diabetes, decreasing insulin resistance or lowering blood pressure comprising administering a hPPARδ agonist. Preferably the hPPARδ agonist is a selective agonist.

In a further aspect there is provided the use of a hPPARδ agonist for the manufacture of a medicament for treating Type 2 diabetes, decreasing insulin resistance or lowering blood pressure. Preferably the hPPARδ agonist is a selective agonist.

In a further aspect the invention provides a method for decreasing fibrinogen levels comprising administering a hPPARδ agonist. Preferably the hPPARδ agonist is a selective agonist.

In a further aspect there is provided the use of a hPPARδ agonist for the manufacture of a medicament for decreasing fibrinogen levels. Preferably the hPPARδ agonist is a selective agonist.

In a further aspect the invention provides a method for decreasing LDLc levels comprising administering a hPPARδ agonist. Preferably the hPPARδ agonist is a selective agonist.

In a further aspect the invention provides the use of a hPPARδ agonist for the manufacture of a medicament for decreasing LDLc levels. Preferably the hPPARδ agonist is a selective agonist.

In a further aspect the invention provides a method for shifting the LDL particle size from small dense to normal dense LDL comprising administering a hPPARδ agonist. Preferably the hPPARδ agonist is a selective agonist.

In a further aspect the invention provides the use of a hPPARδ agonist for the manufacture of a medicament for shifting the LDL particle size from small dense to normal dense LDL. Preferably the hPPARδ agonist is a selective agonist.

As used herein, "a compound of the invention" means a compound of formula (I) or a pharmaceutically acceptable salt or, solvate, thereof.

While hydrolyzable esters and tetrazole derivatives are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably therefore X represents COOH;

Preferably $X^1$ is O, S, or is absent. More preferably $X^1$ represents O.

Preferably $X^2$ is S.

Preferably $R^1$ is H or $CH_3$, more preferably $CH_3$.

Preferably $R^2$ is H.

Preferably Z is N.

Preferably Y is S.

Preferably n is 1.

Preferably y is 1 or 2. When y is 2, preferably one of the substituents is halogen; more preferably one is halogen and the other is $CF_3$. More preferably y is 1. When y is 1, preferably the substituent is in the para position on the ring and is more preferably $CF_3$.

A particular group of compounds is compounds of formula (II), and pharmaceutically acceptable salts, solvates, and hydrolyzable esters thereof, wherein

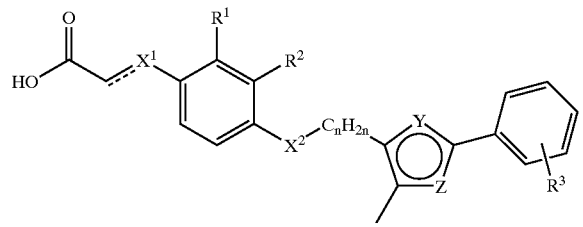

(II)

$X^1$ is NH, $NCH_3$, O, S, a bond (i.e. is absent), $CH_2$, or CH where the dashed line indicates that when $X^1$ is CH the depicted bond is a double bond;

$X^2$ is O or S;

$R^1$ is H, $CH_3$, $OCH_3$, or halogen;

$R^2$ is H, $OCH_3$, or halogen n is 1 or 2;

one of Y and Z is N and the other is S or O.

$R^3$ is H, $CF_3$ or halogen.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferably, the compounds of formula (I) are hPPARδ agonists. As used herein, by "agonist", or "activating compound", or "activator", or the like, is meant those compounds which have a pKi of at least 6.0, preferably at least 7.0, to the relevant PPAR, for example hPPARδ, in the binding assay described below, and which achieve at least 50% activation of the relevant PPAR relative to the appropriate indicated positive control in the transfection assay described below at concentrations of $10^{-5}$ M or less. Preferably, the agonist of this invention achieve 50% activation of human PPARδ in the transfection assay at concentrations of $10^{-7}$ M or less, more preferably $10^{-9}$M or less.

Most preferably, the compounds of formula (I) are selective hPPARδ agonists. As used herein, a "selective hPPARδ agonist" is a hPPARδ agonist whose EC50 for PPARδ is at least 10 fold lower than its EC50 for PPARγ and PPARα. Such selective compounds may be referred to as "10-fold selective." EC50 is defined in the transfection assay described below and is the concentration at which a compound achieves 50% of its maximum activity. Most preferred compounds are greater than 100-fold selective hPPARδ agonists.

The PPARδ selective compounds of this invention elevate HDL-c in db/db mice and primate models and lower fibrinogen in primate models. These PPARδ selective agonists unexpectedly lower triglycerides and insulin levels in the primate.

Since the literature suggests that such triglyceride and fibrinogen lowering effects are due to PPAR alpha agonist activity, it would not be obvious that adding PPAR delta agonist activity to other PPAR activity such as alpha or gamma or alpha/gamma dual activity, would provide any additional triglyceride or fibrinogen lowering benefits. We have surprisingly found that adding PPAR delta activity to other PPAR activity, including PPAR alpha activity, could result in additional triglyceride, LDLc or fibrinogen lowering benefits as well as decreasing insulin resistance.

Preferred compounds of the present invention include:
2-[2-methyl-4-({4-methyl-2-[4-(trifluoromethyl)phenyl]-1,3-oxazol-5-yl}methoxy)phenoxy]acetic acid
3-[2-methyl-4-({4-methyl-2-[4-(trifluoromethyl)phenyl]-1,3-thiazol-5-yl}methoxy)phenyl]propanoic acid
3-[2-methyl-4-({4-methyl-2-[4-(trifluoromethyl)phenyl]-1,3-oxazol-5-yl}methoxy)phenyl]propanoic acid
2-{4-[({4-methyl-2-[4-(trifluoromethyl)phenyl]-1,3-oxazol-5-yl}methyl)sulfanyl]phenyl}acetic acid
2-[2-methyl-4-({4-methyl-2-[4-(trifluoromethyl)phenyl]-1,3-thiazol-5-yl}methoxy)phenoxy]acetic acid
3-[4-({4-methyl-2-[4-(trifluoromethyl)phenyl]-1,3-thiazol-5-yl}methoxy)phenyl]propanoic acid
(E)-3-[2-methyl-4-({4-methyl-2-[4-(trifluoromethyl)phenyl]-1,3-oxazol-5-yl}methoxy)phenyl]-2-propenoic acid
methyl 3-[4-({4-methyl-2-[4-(trifluoromethyl)phenyl]-1,3-thiazol-5-yl}methoxy)phenyl]propanoate
2-{4-[({4-methyl-2-[4-(trifluoromethyl)phenyl]-1,3-thiazol-5-yl}methyl)sulfanyl]phenyl}acetic acid
2-({4-[({4-methyl-2-[4-(trifluoromethyl)phenyl]-1,3-oxazol-5-yl}methyl)sulfanyl]phenyl}sulfanyl)acetic acid
2-[methyl-4-({4-methyl-2-[4-(trifluoromethyl)phenyl]-1,3-thiazol-5-yl}methoxy)anilino]acetic acid
2-{3-chloro-4-[({4-methyl-2-[4-(trifluoromethyl)phenyl]-1,3-oxazol-5-yl}methyl)sulfanyl]phenyl}acetic acid
2-[2-chloro-4-({4-methyl-2-[4-(trifluoromethyl)phenyl]-1,3-oxazol-5-yl}methoxy)phenoxy]acetic acid
2-[3-chloro-4-({4-methyl-2-[4-(trifluoromethyl)phenyl]-1,3-thiazol-5-yl}methoxy)phenyl]acetic acid
2-{4-[({4-methyl-2-[4-(trifluoromethyl)phenyl]-1,3-oxazol-5-yl}methyl)sulfanyl]phenoxy}acetic acid
(E)-3-[4-({4-methyl-2-[4-(trifluoromethyl)phenyl]-1,3-oxazol-5-yl}methoxy)phenyl]-2-propenoic acid
2-[4-({4-methyl-2-[4-(trifluoromethyl)phenyl]-1,3-oxazol-5-yl}methoxy)phenoxy]acetic acid
2-[3-fluoro-4-({4-methyl-2-[4-(trifluoromethyl)phenyl]-1,3-thiazol-5-yl}methoxy)phenyl]acetic acid
methyl 2-[3-chloro-4-({4-methyl-2-[4-(trifluoromethyl)phenyl]-1,3-oxazol-5-yl}methoxy)phenyl]acetate
2-{2-methyl-4-[({4-methyl-2-[4-bromophenyl]-1,3-thiazol-5-yl)methyl)sulfanyl]phenoxy}acetic acid
ethyl 2-{2-methyl-4-[({4-methyl-2-[4-bromophenyl]-1,3-thiazol-5-yl}methyl) sulfanyl]phenoxy}acetate
2-{2-methyl-4-[({4-methyl-2-[4-chlorophenyl]-1,3-thiazol-5-yl}methyl)sulfanyl]phenoxy}acetic acid
ethyl 2-{2-methyl-4-[({4-methyl-2-[4-chlorophenyl]-1,3-thiazol-5-yl}methyl) sulfanyl]phenoxy}acetate
2-{2-methyl-4-[({4-methyl-2-[4-fluorophenyl]-1,3-thiazol-5-yl}methyl)sulfanyl]phenoxy}acetic acid
ethyl 2-{2-methyl-4-[({4-methyl-2-[4-fluorophenyl]-1,3-thiazol-5-yl}methyl)sulfanyl]phenoxy}acetate
2-{2-methyl-4-[({4-methyl-2-[3,4-difluorophenyl]-1,3-thiazol-5-yl}methyl)sulfanyl]phenoxy}acetic acid
ethyl 2-{2-methyl-4-[({4-methyl-2-[3,4-difluorophenyl]-1,3-thiazol-5-yl}methyl)sulfanyl]phenoxy}acetate
2-{2-methyl-4-[({4-methyl-2-[3,4-dichlorophenyl]-1,3-thiazol-5-yl}methyl)sulfanyl]phenoxy}acetic acid
ethyl2-{2-methyl-4-[({4-methyl-2-[3,4-dichlorophenyl]-1,3-thiazol-5-yl}methyl)sulfanyl]phenoxy}acetate
2-{2-methyl-4-[({4-methyl-2-[3,5-bis(trifluoromethyl)phenyl]-1,3-thiazol-5-yl}methyl)sulfanyl]phenoxy}acetic acid
ethyl 2-{2-methyl-4-[({4-methyl-2-[3,5-bis(trifluoromethyl)phenyl]-1,3-thiazol-5-yl}methyl)sulfanyl]phenoxy}acetate
ethyl 2-{2-methyl-4-[({4-methyl-2-[3-fluoro-4-(trifluoromethyl)phenyl]-1,3-thiazol-5-yl}methyl)sulfanyl]phenoxy}acetate
5-[4-({4-methyl-2-[4-(trifluoromethyl)phenyl]-1,3-oxazol-5-yl}methoxy)phenoxymethyl]-2H-tetrazole
5-[4-({4-methyl-2-[4-(trifluoromethyl)phenyl]-1,3-oxazol-5-yl}methoxy)benzyl]-2H-tetrazole
5-[4-({4-methyl-2-[4-(trifluoromethyl)phenyl]-1,3-thiazol-5-yl}sulfanyl)benzyl]-2H-tetrazole
5-[4-({4-methyl-2-[4-(trifluoromethyl)phenyl]-1,3-oxazol-5-yl}sulfanyl)benzyl]-2H-tetrazole
5-[2-methyl-4-({4-methyl-2-[4-(trifluoromethyl)phenyl]-1,3-thiazol-5-yl}methoxy)benzyl]-2H-tetrazole
5-[2-methyl-4-({4-methyl-2-[4-(trifluoromethyl)phenyl]-1,3-thiazol-5-yl}sulfanyl)benzyl]-2H-tetrazole More preferred compounds of the invention are:
2-{2-methyl-4-[({4-methyl-2-[4-(trifluoromethyl)phenyl]-1,3-thiazol-5-yl}methyl)sulfanyl]phenoxy}acetic acid
2-{2-methyl-4-[({4-methyl-2-[4-(trifluoromethyl)phenyl]-1,3-oxazol-5-yl}methyl)sulfanyl]phenoxy}acetic acid
methyl 2-{4-[({4-methyl-2-[4-(trifluoromethyl)phenyl]-1,3-thiazol-5-yl}methyl)sulfanyl]phenoxy}acetate
2-{4-[({4-methyl-2-[4-(trifluoromethyl)phenyl]-1,3-thiazol-5-yl}methyl)sulfanyl]phenoxy}acetic acid
(E)-3-[2-methyl-4-({4-methyl-2-[4-(trifluoromethyl)phenyl]-1,3-thiazol-5-yl}methoxy)phenyl]-2-propenoic acid
2-{3-chloro-4-[({4-methyl-2-[4-(trifluoromethyl)phenyl]-1,3-thiazol-5-yl}methyl)sulfanyl]phenyl}acetic acid
2-{2-methyl-4-[({4-methyl-2-[3-fluoro-4-(trifluoromethyl)phenyl]-1,3-thiazol-5-yl}methyl)sulfanyl]phenoxy}acetic acid A particularly preferred compound of the invention is:
2-{2-methyl-4[({4-methyl-2-[4-(trifluoromethyl)phenyl]-1,3-thiazol-5-yl}methyl)sulfanyl]phenoxy}acetic acid.

All the preferred and most preferred compounds listed above are selective hPPARδ agonists.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of formula (I) or a pharmaceutically acceptable salt or solvate thereof together with one or more pharmaceutically acceptable carriers therefor and, optionally, other therapeutic and/or prophylactic ingredients.

Formulations of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas, or PPAR gamma, PPAR alpha and PPAR alpha/gamma agonists (for example thiazolidinediones such as e.g. Pioglitazone and Rosiglitazone). The compounds may also be used in combination with antihypertensive agents such as angiotensin antagonists eg telmisartan, calcium channel antagonists eg lacidipine and ACE inhibitors eg enalapril. The invention thus provides in a further aspect the use of a combination comprising a compound of formula (I) with a further therapeutic agent in the treatment of a hPPAR delta mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same disease, the dose of each compound may differ from that when the compound is used alone. Appropriate doses will be readily appreciated by those skilled in the art.

Compounds of this invention may be conveniently prepared by a general process wherein a moiety like A is coupled to an alcohol (B) using the Mitsunobu protocol (O. Mitsunobu, 1981 Synthesis, p 1) or by alkylation of A using a suitable non nucleophilic base such as $K_2CO_3$, $Cs_2CO_3$ or NaH, with an alkyl halide (C). Note that this synthesis is preferably carried out with the acid group protected by R. Preferably, R is 1–6 alkyl which can be hydrolyzed off to give an acid of Formula (I), or if readily hydrolyzable, the resulting ester can be administered.

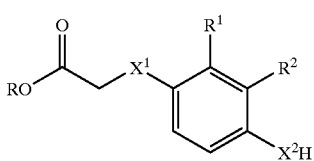
A

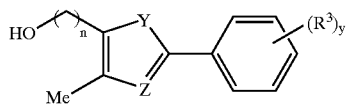
B

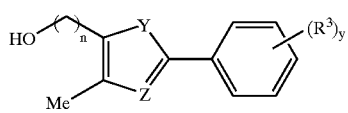
C

For example, when n is 1, Y is S, Z is N, and $R^3$ is para-$CF_3$:

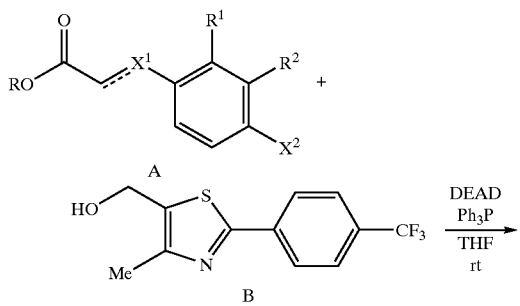

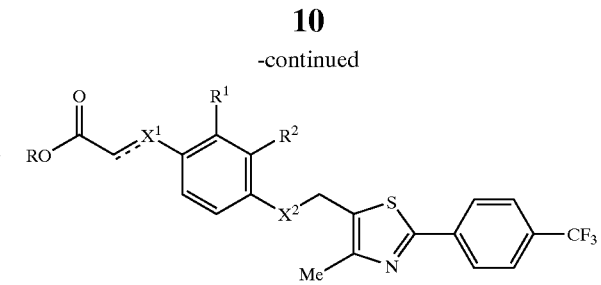

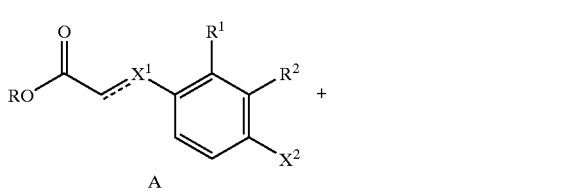
A

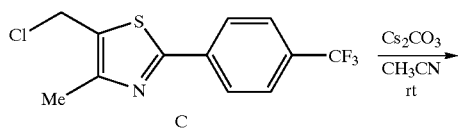
C

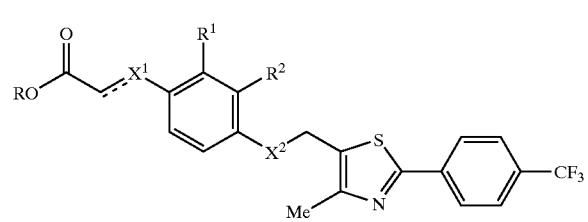

Some of the intermediates of type A are commercially available while others can be synthesized as outlined below. The synthesis of intermediates of type B is also illustrated below.

Furthermore, the tetrazole derivatives may be conveniently prepared by a general process wherein a moiety like D is coupled to an alcohol (B) using the Mitsunobu protocol (O. Mitsunobu, 1981 Synthesis, p 1), by alkylation of D using a suitable non nucleophilic base such as $K_2CO_3$, $Cs_2CO_3$ or NaH, with an alkyl halide (C) or by coupling of a moiety like E with an alkyl halide (C) using a suitable non nucleophilic base such as NaOH.

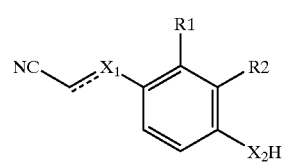
D

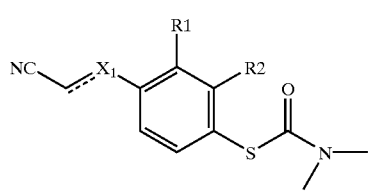
E

For example, when n is 1, Y is S, Z is N, and $R^3$ is para-$CF_3$:

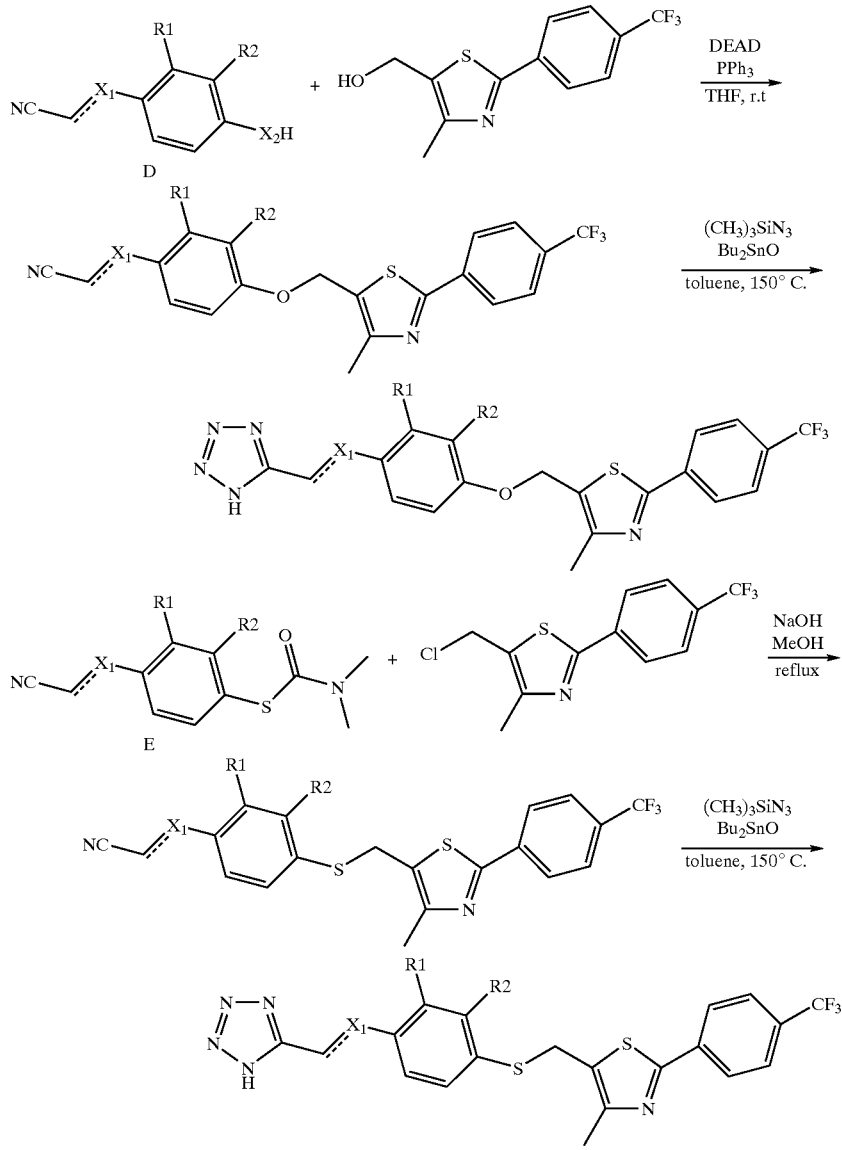

The invention is further illustrated by the following Intermediates and Examples which should not be construed as constituting a limitation thereto.

Intermediates

Intermediate 1

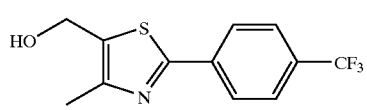

To a well stirred solution of LiAlH$_4$ (1.52 g, 40 mmol) in dry THF (50 mL) at 0° C., was slowly added a solution of ethyl 4-methyl-2-[4-(trifluoromethyl)phenyl]-thiazole-5-carboxylate (12.6 g, 40 mmol) in dry THF (50 mL). The mixture was stirred at room temperature for 2 hs. The reaction was quenched by slow addition at 0° C. of water (2 mL), 5N NaOH (2 mL) and water (6 mL). The precipitate was filtered, washed with EtOAc, MeOH, CH$_2$Cl$_2$ and THF. After evaporation, a yellow solid was obtained, that was crystallyzed from MeOH-water to afford intermediate 1 depicted above (9.90 g, 36 mmol, 90%) as a yellow solid mp 120–122° C.

Intermediate 2

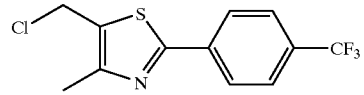

To a cold (0° C.) stirred solution of intermediate 1 (8.2 g, 30 mmol) and Et$_3$N (6.07 g, 8.36 mL, 60 mmol), in dry CH$_2$Cl$_2$ (120 mL) was slowly added MeSO$_2$Cl (5.49 g, 3.71 mL, 48 mmol). After 2 hs at 0° C. more Et$_3$N (6 mmol) and MeSO$_2$Cl (4.8 mmol) were added. After 2 more h a tic (hexane:EtOAc, 1:1) showed complete reaction. The reaction mixture was diluted with CH$_2$Cl$_2$ (120 mL) and washed with NaHCO$_3$ (sat.) (2×240 mL) and water (2×240 mL), dried, filtered and evaporated to afford intermediate 2 (8.0 g, 27 mmol, 90%) as a yellow solid.

Intermediate 3

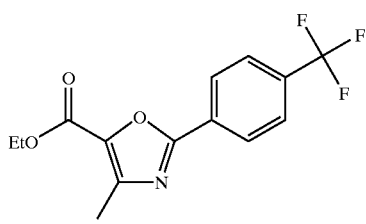

A neat mixture of methyl 2-chloroacetoacetate (9.88 g, 8.0 mL, 65.6 mmol) and 4-(trifluoromethyl)benzamide acid (5.67 g, 30 mmol), was heated in an oil bath at 120° C. for 48 h. The dark mixture was cooled down to room temperature and diluted with EtOAc (100 mL) and succesively washed with: NaHCO3 (sat.) (3×100 mL) and water (3×100 mL), dried, filtered and evaporated to a syrup. The syrup was dissolved in acetone and precipitated with hexane. The solids (unreacted 4-(trifluoromethyl)benzamide acid were filtered and washed with more hexane. The solution was evaporated under vacuum at 60° C. to eliminate traces of methyl 2-chloroacetoacetate. The resulting mixture was purified by flash column chromatography (hexane:EtOAc, 95:5), to afford intermediate 3 (2.2 g, 7.7 mmol, 25%) as a white solid.

Intermediate 4

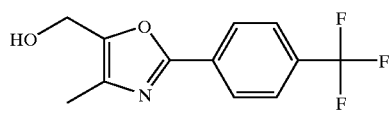

To a well stirred solution of LiAlH$_4$ (213 mg, 5.6 mmol) in dry THF (7.0 mL) at 0° C., was slowly added a solution of intermediate 3 (1.6 g, 5.6 mmol) in dry THF (7.0 mL). The mixture was stirred at room temperature for 2 h. The reaction was quenched by slow addition at 0° C. of water (0.3 mL), 5N NaOH (0.3 mL) and water (0.9 mL). The precipitate was filtered, washed with EtOAc, MeOH, CH$_2$Cl$_2$ and THF. After evaporation, intermediate 4 (1.1 g, 4.3 mmol, 77%) was obtained as a yellow solid.

Intermediate 5

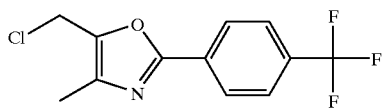

To a cold (0° C.) stirred solution of intermediate 4 (2.57 g, 10 mmol) and Et$_3$N (2.02 g, 2.78 mL, 20 mmol), in dry CH$_2$Cl$_2$ (40 mL) was slowly added MeSO$_2$Cl (1.83 g, 1.24 mL, 16 mmol). After 2 h at 0° C. more Et$_3$N (4 mmol) and MeSO$_2$Cl (3.2 mmol) were added. After 2 more h a tlc (hexane:EtOAc, 1:1), showed complete reaction. The reaction mixture was diluted with CH$_2$Cl$_2$ (40 mL) and washed with NaHCO$_3$ (sat.) (2×80 mL) and water (2×80 mL), dried, filtered and evaporated to afford intermediate 5 (2.8 g, 10 mmol, 100%) as a yellow solid.

Intermediate 6

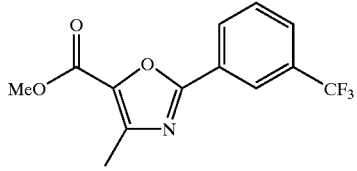

A solution of 3-(trifluoromethyl)benzoic acid (570 mg, 3.0 mmol) in dry DMF (10 mL) was heated at 55° C. Solid K$_2$CO$_3$ (220 mg, 1.53 mmol) was added, followed by methyl 2-chloroacetoacetate (452 mg, 3.0 mmol). The suspension was stirred for 1.5 h at 55° C. The reaction was then partitioned between water (40 mL) and ether (50 mL). The organic layer was further washed with brine (2×40 mL), dried, filtered and evaporated to a yellow oil. A solution of this oil in AcOH (10 mL), was added to a suspension of NH$_4$OAc (0.64 g, 8.3 mmol) in dry toluene (10 mL). The reaction was then refluxed overnight. It was poured into ice/water (60 mL) and extracted with ether (4×30 mL). The organic layer was washed with brine (2×60 mL), dried, filtered and evaporated to give crude material that was purified by flash column chromatography (CH$_2$Cl$_2$) to afford intermediate 6 (320 mg, 1.12 mmol, 37%) as a white solid.

Intermediate 7

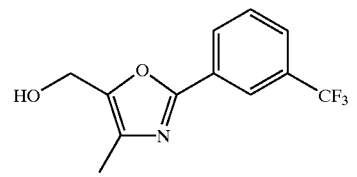

To a well stirred solution of LiAlH$_4$ (38 mg, 1.0 mmol) in dry THF (1.5 mL) at 0° C., was slowly added a solution of intermediate 6 (285 mg, 1.0 mmol) in dry THF (1.5 mL). The mixture was stirred at room temperature for 2 h. The reaction was quenched by slow addition at 0° C. of water (100 μL), 5N NaOH (100 μL) and water (300 μL). The precipitate was filtered, washed with EtOAc, MeOH, CH$_2$Cl$_2$ and THF to afford intermediate 7 (210 mg, 0.82 mmol, 82%) as a white solid.

Intermediate 8

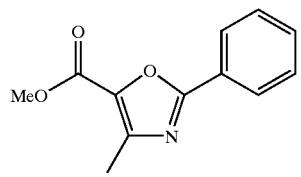

A solution of benzoic acid (1.22 g, 10.0 mmol) in dry DMF (20 mL) was heated at 55° C. Solid K$_2$CO$_3$ (691 mg, 5.0 mmol) was added, followed by methyl 2-chloroacetoacetate (1.50 g, 10.0 mmol). The suspension was stirred for 1.5 h at 55° C. The reaction was then partitioned between water (150 mL) and ether (150 mL). The organic layer was further washed with brine (2×150 mL), dried, filtered and evaporated to a yellow oil. A solution of this oil in AcOH (20 mL), was added to a suspension of NH$_4$OAc (2.13 g, 28 mmol) in dry toluene (20 mL). The reaction was then refluxed overnight. It was poured into ice/water (200 mL) and extracted with ether (4×100 mL). The organic layer was washed with brine (2×200 mL), dried, filtered and evaporated to give crude material that was purified by flash column chromatography (hexane:EtOAc, 4:1) to afford intermediate 8 (720 mg, 3.13 mmol, 32%) as a white solid Intermediate 9

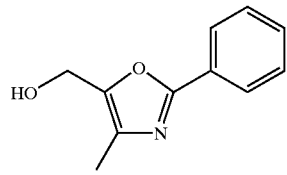

To a well stirred solution of LiAlH$_4$ (76 mg, 2.0 mmol) in dry THF (2.5 mL) at 0° C., was slowly added a solution of intermediate 8 (434 mg, 2.0 mmol) in dry THF (2.5 mL). The mixture was stirred at room temperature for 2 h. The reaction was quenched by slow addition at 0° C. of water (100 μL), 5N NaOH (100 μL) and water (300 μL). The precipitate was filtered, washed with EtOAc, MeOH, CH$_2$Cl$_2$ and THF to afford intermediate 9 (349 mg, 0.92 mmol, 46%). Which was used without further purification.

Intermediate 10

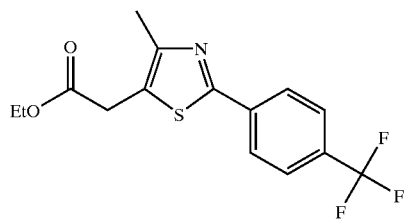

A solution of ethyl-3-bromo4-oxopentanoate (670 mg, 3.0 mmol) and 4-(trifluoromethyl)thiobenzamide (677 mg, 3.3 mmol) in EtOH (5 mL) was refluxed overnight. After cooling to room temperature the solution was diluted with AcOEt. After adding hexane a precipitate appeared. It was filtered and washed with hexane to afford intermediate 10 (300 mg, 0.91 mmol) as a white solid. The mother liquors were evaporated to a syrup that was purified by flash column chromatography (hexane:EtOAc, 9:1) to afford additional intermediate 10 (300 mg, 0.91 mmol). Total yield was 60%.

Intermediate 11

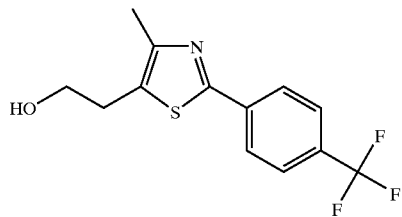

To a well stirred solution of LiAlH$_4$ (31 mg, 0.8 mmol) in dry THF (1.0 mL) at 0° C., was slowly added a solution of intermediate 10 (264 mg, 0.8 mmol) in dry THF (1.5 mL) and dry CH$_2$Cl$_2$ (1.5 mL). The mixture was stirred at room temperature for 2 h. The reaction was quenched by slow addition at 0° C. of water (50.0 μL), 5N NaOH (50.0 μL) and water (150 μL). The precipitate was filtered, washed with EtOAc, MeOH, CH$_2$Cl$_2$ and THF. After evaporation intermediate 11 (133 mg, 0.46 mmol, 57%) was obtained as a yellow solid.

Intermediate 12

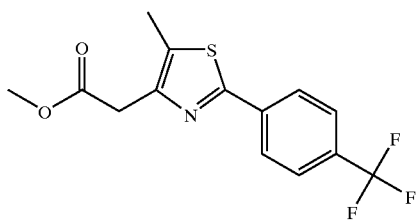

A solution of methyl-4-bromo-3-oxopentanoate (890 mg, 4.0 mmol) and and 4-(trifluoromethyl)thiobenzamide (820 mg, 4.0 mmol) in EtOH (10 mL) was refluxed overnight. After cooling to room temperature the solution was diluted with AcOEt and successively washed with (sat.) NaHCO$_3$ (3×50 mL) and brine (2×50 mL), dried, filtered, and evaporated to dryness. A yellow solid was obtained, that was purified by flash column chromatography (hexane:EtOAc, 1:1) to afford the title compound (1.32 g, 4.0 mmol, 100%) as a white solid.

Intermediate 13

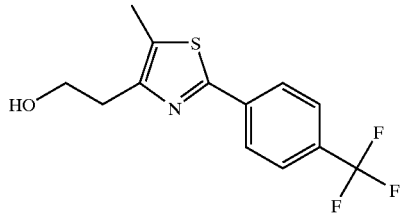

To a well stirred solution of LiAlH$_4$ (76 mg, 2.0 mmol) in dry THF (2.5 mL) at 0° C., was slowly added a solution of Intermediate 12 (659 mg, 2.0 mmol) in dry THF (2.5 mL). The mixture was stirred at room temperature for 2 h. The reaction was quenched by slow addition at 0° C. of water (100 μL), 5N NaOH (100 μL) and water (300 μL). The precipitate was filtered, washed with EtOAc, MeOH, CH$_2$Cl$_2$ and THF. After evaporation compound the title compound was obtained as a yellow solid (472 mg, 1.64 mmol, 82%).

Intermediate 14

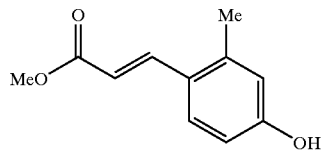

Methyl acrylate and 4-bromo-3-methylphenol were coupled using Heck conditions as described in the general procedure 4. The crude material was crystallized from acetone:hexane to afford the title compound (40%) as an amorphous solid.

Intermediate 15

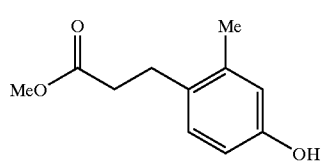

A solution of intermediate 14 (1.92 g, 10 mmol) in EtOAc (50 mL) was hydrogenated at 50–60 psi at room temperature, in the presence of Pd/C 10% (500 mg). After 15 min., the mixture was filtered through celite, washed with additional EtOAc and evaporated to afford the title compound (1.94 g, 10 mmol, 100%) as a colorless syrup.

Intermediate 16

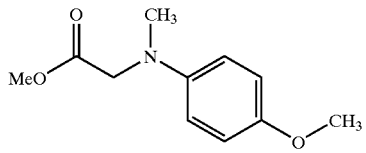

N-Methylanisidine (2.0 g, 15 mmol),methyl bromoacetate (2.25 g, 15 mmol), DMAP (0.04 g, 2% by wt), and Net₃ (2.25 g, 15 mmol) in EtOH (50 mL) was refluxed for 1 h. The solvents were evaporated. The remaining residue was chromatographied on a silica gel column with 10% EtOAc in hexanes to afford the title compound (70%) as a yellow oil: NMR (DMSO-d6) δ2.97 (s, 3H), 3.66(s, 3H), 3.72 (s,3H), 4.18 (s,2H), 6.68(d, 2H), 6.85(d, 2H)

MS m/z 210 (M+1)

Intermediate 17

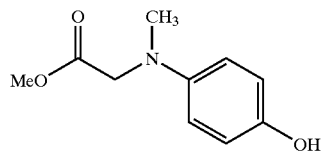

Intermediate 16 (1.9 g, 9.0 mmol) in CH₂Cl₂ (10 mL) was added to 1M BBr₃ in CH₂Cl₂ (28 mL) slowly at 0° C. The resulting solution was stirred at low temperature for 2 h, and poured onto ice-water. The mixture was extracted with CH₂Cl₂ (2×50 mL), dried, and evaporated. A solution of this residue and acetyl chloride(1.4 g, 18 mmol) in MeOH was refluxed for 18 h. The solvents were evaporated. The residue was chromatographed over silica gel to afford the title compound (45%)as a yellow oil: NMR (MeOH-d4) δ3.39 (s, 3H), 3.72(s, 3H), 4.51 (s,2H),6.87(d, 2H), 7.48 (d, 2H)

MS m/z 196(M+1)

Intermediate 18

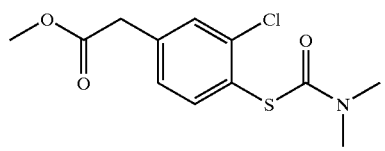

Methyl 3-Chloro-4-hydroxyphenylacetate was treated with dimethyl thiocarbamoyl chloride as described in general procedure 5 to afford, after column chromatography (hexane:EtOAc, 4:1), a brown oil (95%). The residue was refluxed in tetradecane as to afford after column chromatography (hexane:EtOAc, 4:1) the title compound (77%) as a yellow oil.

Intermediate 19

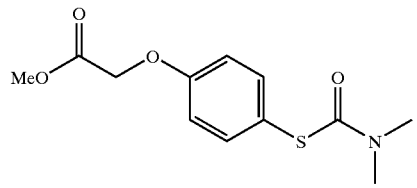

Methyl 2-(4-hydroxyphenoxy)acetate was treated with dimethyl thiocarbamoyl chloride as described in general procedure 5 to afford, after column chromatography (hexane:EtOAc, 4:1), (84%) as a yellow oil. The oil was refluxed in tetradecane as to afford after column chromatography (hexane:EtOAc, 4:1) the title compound (53%) as a yellow oil.

Intermediate 20

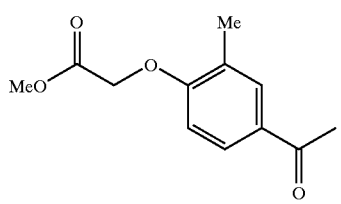

A mixture of methyl bromoacetate (3.80 g, 2.35 mL, 25.0 mmol), 4-hydroxy-3-methylacetophenone (4.13 g, 27.5 mmol), and Cs₂CO₃ (17.9 g, 55 mmol) in dry acetonitrile (125 mL) was stirred overnight at r.t. The mixture was filtered, washed with acetonitrile, and the solvent evaporated. The remaining syrup was redissolved in EtOAc (400 mL), washed with 1 N NaOH (3×400 mL) and water (2×400 mL), dried, filtered, and evaporated to afford the pure title compound (5.50 g, 24.7 mmol, 99%) as a white solid.

Intermediate 21

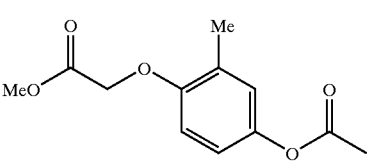

A solution of Intermediate 20 (5.33 g, 24 mmol), mCPBA (7.25 g, 42 mmol) and p-TsOH (480 mg) in dry dichloromethane (120 mL) was refluxed for 48 h. The reaction mixture was diluted with dichloromethane (120 mL), and successively washed with: aq. KI (2×200 mL), NaHSO₃ (2×200 mL), dried, filtered and evaporated to afford the title compound (5.0 g, 21 mmol, 87%) as a syrup.

Intermediate 22

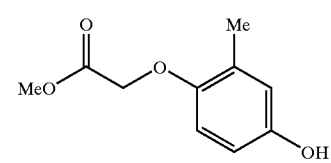

A solution of intermediate 21 (4.76 g, 20 mmol) in dry methanol (180 mL) was treated with a 0.5 N solution of NaOCH₃ in MeOH (40 mL, 20 mmol). After 1 h at r.t., the solution was neutralized with 1 N HCl (20 mL). The solvent was evaporated, and the residue partitioned between dichloromethane (300 mL) and water (300 mL). The organic solution was separated, washed with water (300 mL), dried, filtered, and evaporated to afford the title compound (3.3 g, 16.8 mmol, 84%) as a brown solid.

Intermediate 23

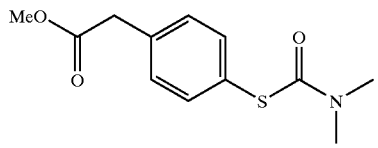

Methyl 4-hydroxyphenylacetate was treated with dimethyl thiocarbamoyl chloride as described in general procedure 5 to afford, after column chromatography (hexane:EtOAc, 4:1) (90%) a yellow solid. The solid was refluxed in tetradecane to afford after column chromatography (hexane:EtOAc, 4:1) the title compound (74%) as a brown oil.

Intermediate 24

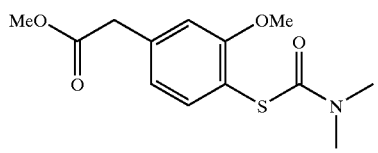

Methyl 3-methoxy-4-hydroxyphenylacetate was treated with dimethyl thiocarbamoyl chloride as described in general procedure 5 to afford, after column chromatography (hexane:EtOAc, 4:1), a brown oil (95%). The oil was refluxed in tetradecane to afford after column chromatography (hexane:EtOAc, 4:1) compound the title compound (17%) as a yellow oil.

Intermediate 25

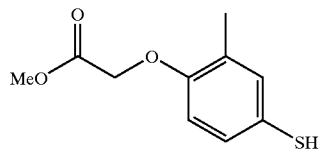

Intermediate 22 was treated with dimethyl thiocarbamoyl chloride as described in general procedure 5 to afford a dark oil (100%). The dark oil was refluxed in tetradecane to afford after column chromatography (hexane:EtOAc, 2:1) compound a brown solid (47%). The brown solid was treated with NaOMe/HOMe to afford, after column chromatography (hexane:EtOAc, 4:1), compound the title compound (34%) as a colorless syrup.

General Procedure A for the Preparation of Substituted Thiobenzamides

To a solution of $P_4S_{10}$ (0.2 mmol) in toluene (100 mL) was added $NaHCO_3$ (2 mmol) and the mixture heated to reflux for ca. 30 min. The substituted benzamide (1 mmol) was added and the reaction stirred at 90° C. for 1 h. The reaction was then evaporated to dryness, treated with brine (100 mL) and extracted with $CH_2Cl_2$ (2×50 mL). The organic phase dried, filtered, and evaporated to afford the final product.

Intermediate 26

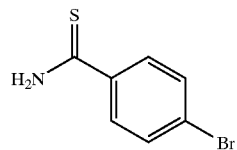

The title compound was prepared as described in general procedure A to afford an orange solid (88%).

MS m/z 217 (M+1)

Intermediate 27

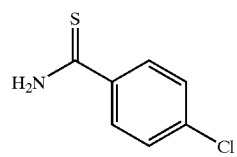

The title compound was prepared as described in general procedure A to afford an orange solid (99%).

MS m/z 171

Intermediate 28

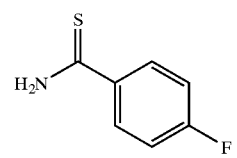

The title compound was prepared as described in general procedure A to afford an orange solid (58%).

MS m/z 155

Intermediate 29

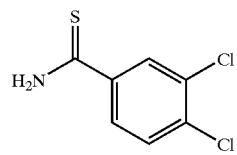

The title compound was prepared as described in general proceedure A to afford a yellow solid (87%).

MS m/z 207 (M+1)

Intermediate 30

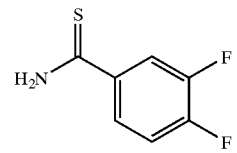

The title compound was prepared as described in general procedure A to afford a brownish orange solid (78%).

MS m/z 173

Intermediate 31

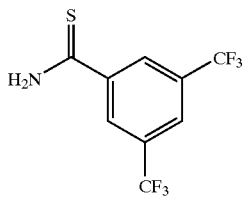

The title compound was prepared as described in general procedure A to afford a yellow semi-solid (55%).

MS m/z 273

Intermediate 32

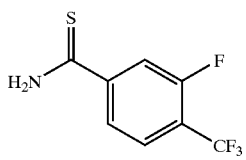

The title compound was prepared as described in general procedure A to afford a yellow solid (50%).

MS m/z 223

General Procedure B for the Preparation of 2-substituted phenyl4-methyl-1,3-thiazole-5-caboxylic Acid Ethyl Esters To a solution of the substituted thiobenzamide (1 mmol) in EtOH (100 mL) was added ethyl 2-chloroacetoacetate (1.1 mmol) and the mixture heated to reflux overnight. The reaction is cooled to room temperature and the solvent evaporated. The solid is crystallized from Et$_2$O or hexane to afford the final product.

Intermediate 33

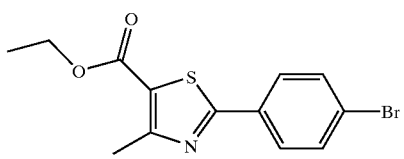

Intermediate 26 was reacted as described in general procedure B to afford the title compound as an off-white solid (41%).

MS m/z 327 (M+1)

Intermediate 34

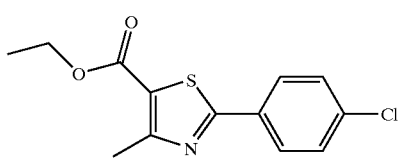

Intermediate 27 was reacted as described in general procedure B to afford the title compound as an off-white solid (29%).

MS m/z 281

Intermediate 35

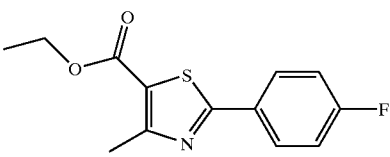

Intermediate 28 was reacted as described in general procedure B to afford the title compound as an off-white solid (25%).

1H-NMR (CDCl3) δ1.35 (t, 3H), 2.75 (s, 3H), 4.35 (q, 2H), 7.15 (t, 2H), 7.95 (dd, 2H).

Intermediate 36

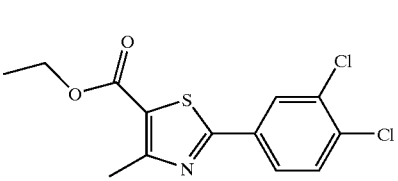

Intermediate 29 was reacted as described in general procedure B to afford the title compound as an off-white solid (46%).

MS m/z 315

Intermediate 37

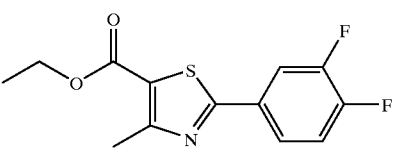

Intermediate 30 was reacted as described in general procedure B to afford the title compound as an off-white solid (41%).

1H-NMR (CDCl3) δ1.35 (t, 3H), 2.75 (s, 3H), 4.35 (q, 2H), 7.25 (dd, 1H), 7.65 (m, 1H), 7.75 (ddd, 1H).

Intermediate 38

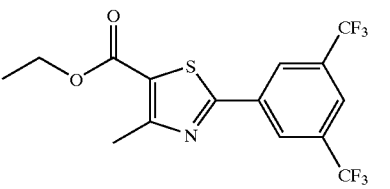

Intermediate 31 was reacted as described in general procedure B to afford the title compound as an off-white solid (58%).

MS m/z 383

Intermediate 39

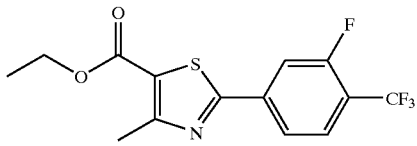

Intermediate 32 was reacted as described in general procedure B to afford the title compound as an off-white solid (56%).

MS m/z 333

General Procedure C for the Preparation of 2-substituted phenyl-5-hydroxymethyl-4-methyl-1,3-thiazoles To a solution of LiAlH$_4$ (2 mmol) in THF (100 mL) at 0° C. was added the 2-substituted phenyl-4-methyl-1,3-thiazole-5-caboxylic acid ethyl ester. The reaction is stirred while it is allowed to warm to rt. After all the starting material has disappeared, the reaction is cautiously treated with water (5 mL) followed by 1N NaOH (10 mL). The mixture was filtered through celite. The filtrate was extracted with CH$_2$Cl$_2$ (3×50 mL). The organic phase was dried, filtered and evaporated to afford the final product.

Intermediate 40

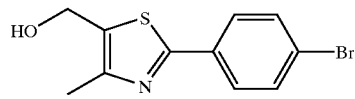

Intermediate 33 was reacted as described in general procedure C to afford the title compound as an off-white solid (75%).

MS m/z 285 (M+1)

Intermediate 41

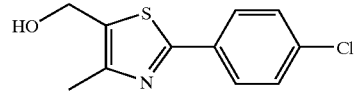

Intermediate 34 was reacted as described in general procedure C to afford the title compound as an off-white solid (87%).

MS m/z 239

Intermediate 42

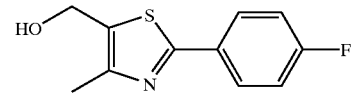

Intermediate 35 was reacted as described in general procedure C to afford the title compound as an off-white solid (89%).

1H-NMR (CDCl3) δ1.7 (bs, 1H), 2.35 (s, 3H), 4.75 (s, 2H), 7.05 (t, 2H), 7.80 (dd, 2H).

Intermediate 43

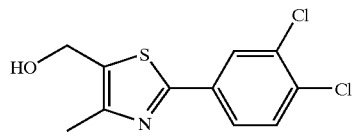

Intermediate 36 was reacted as described in general procedure C to afford the title compound as an off-white solid (56%).

MS m/z 275 (M+1)

Intermediate 44

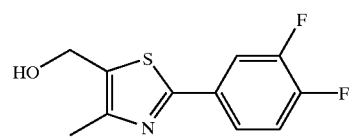

Intermediate 37 was reacted as described in general procedure C to afford the title compound as an off-white solid (52%).

MS m/z 241

Intermediate 45

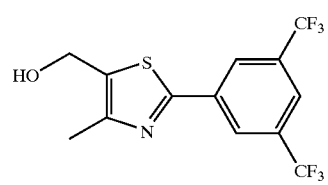

Intermediate 38 was reacted as described in general procedure C to afford the title compound as an off-white solid (27%).

MS m/z 341

Intermediate 46

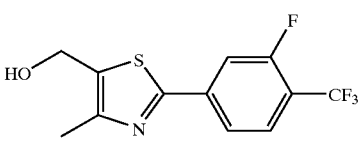

Intermediate 39 was reacted as described in general procedure C to afford the title compound as an off-white solid (63%).

MS m/z 291

General Procedure D for the Preparation of 2-substituted phenyl-5-chloromethyl-4-methyl-1,3-thiazoles To a solution of the 2-substituted phenyl-5-hydroxymethyl-4-methyl-1,3-thiazole (1 mmol) and Et$_3$N (2 mmol) in CH$_2$Cl$_2$ (100 mL) at 0° C. was added dropwise methanesulfonyl chloride (1.6 mmol). After 2–4 h the reaction was complete. CH$_2$Cl$_2$ (50 mL) is added and the organic phase washed with a saturated. NaHCO$_3$ solution (2×50 mL), water (2×50 mL), dried, filtered and then evaporated to afford the final product.

Intermediate 47

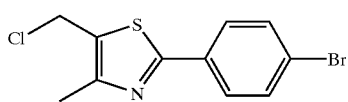

Intermediate 40 was reacted as described in general procedure D to afford the title compound as an white solid (40%).

MS m/z 303

Intermediate 48

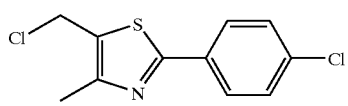

Intermediate 41 was reacted as described in general procedure D to afford the title compound as an white solid (80%).

MS m/z 259 (M+1)

Intermediate 49

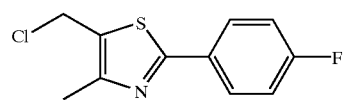

Intermediate 42 was reacted as described in general procedure D to afford the title compound as a pale yellow solid (100%).

MS m/z 241

Intermediate 50

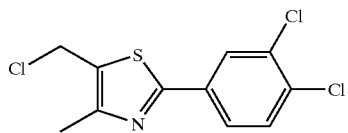

Intermediate 43 was reacted as described in general procedure D to afford the title compound as a pale yellow solid (74%).

1H-NMR (CDCl3) δ2.40 (s, 3H), 4.70 (s, 2H), 7.40 (dd, 1H), 7.60 (dd, 1H), 7.90 (d, 1H).

Intermediate 51

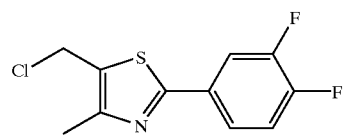

Intermediate 44 was reacted as described in general procedure D to afford the title compound as a pale yellow solid (83%).

1H-NMR (CDCl3) δ2.30 (s, 3H), 4.60 (s, 2H), 7.00 (dd, 1H), 7.40 (m, 1H), 7.50 (m, 1H).

Intermediate 52

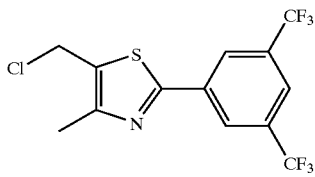

Intermediate 45 was reacted as described in general procedure D to afford the title compound as a pale yellow solid (100%).

1H-NMR (CDCl3) δ2.40 (s, 3H), 4.70 (s, 2H), 7.80 (s, 1H), 8.30 (s, 2H).

Intermediate 53

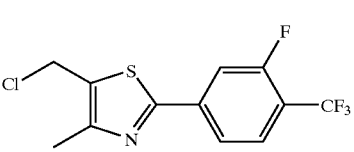

Intermediate 46 was reacted as described in general procedure D to afford the title compound as a pale yellow solid (100%).

1H-NMR (CDCl3) δ2.40 (s, 3H), 4.70 (s, 2H), 7.55–7.75 (m, 3H).

Intermediate 54

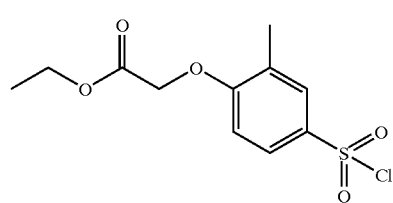

Chlorosulfonic acid (15 mL) was cooled to 0° C. then 10.0 g (0.05M) of ethyl (2-methylphenoxyacetate was added over 10 m. The reaction mixture was stirred at 0–5° C. for 30 m, the bath was removed and stirring continued for 2 h. The reaction mixture was poured into ice, forming a white solid which was washed with ice water and dried under high vacuum affording the title compound (12.846 g, 86%).

Intermediate 55

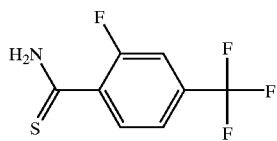

2-Fluoro-4-(trifluoromethyl)benzenecarbothioamide

To a solution of 2-fluoro-4-(trifluoromethyl)benzonitrile (5.2 g, 27.5 mmol) in 50 ml methanol was added 10 ml of water and NaSH×H2O (7.71 g, 137.5 mmol). After heating at 50° C. for 12 hours, the solvent was removed in vacuo and the residue treated with water (200 ml) and extracted with ethyl acetate (2×150 ml).

The organic layers were dried (MgSO4) and the solvent evaporated to give crude residue which was purified by Biotage FlashElute with a 40M silica cartridge and eluting with hexanes/ethyl acetate (4:1)

To yield 3.27 g (53%) of 2-fluoro-4-(trifluoromethyl) benzenecarbothioamide, intermediate 55 as a yellow solid. MS m/z 223 (M+1)

Intermediate 56

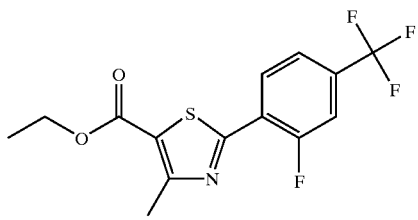

Intermediate 55 was reacted as described in general procedure B to afford the title compound as a light yellow solid (71%)

MS m/z 333 (M+1)

Intermediate 57

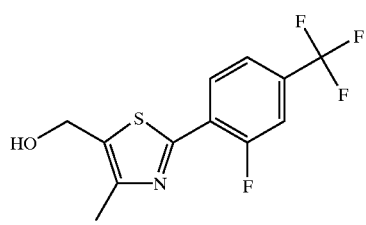

Intermediate 56 was reacted as described in general procedure C to afford the title compound as a light yellow solid (83%)

MS m/z 291 (M+1)

Intermediate 58

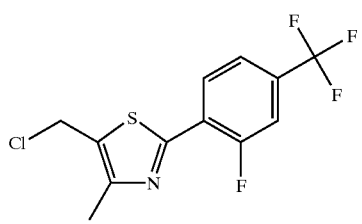

Intermediate 57 was reacted as described in general procedure D to afford the title compound as a light yellow solid (100%)

Rf of starting alcohol in 3:1 hexanes/ethyl acetate is 0.25

Rf of chloride in 3:1 hexanes/ethyl acetate is 0.75

Intermediate 59

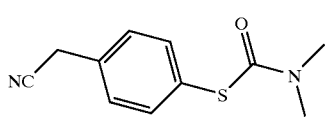

4-hydroxybenzyl cyanide was treated with dimethyl thiocarbamoyl chloride as described in general procedure 5 to afford, after column chromatography (DCM), a yellow solid (78%). The solid was refluxed in tetradecane as to afford after column chromatography (DCM:MeOH) the title compound (40%) as an off-white solid.

Intermediate 60

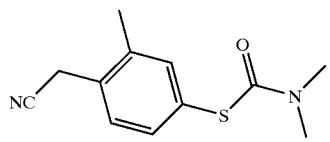

4-hydroxy-2-methylbenzyl cyanide was treated with dimethyl thiocarbamoyl chloride as described in general procedure 5 to afford, after column chromatography (DCM), a yellow solid (48%). The solid was refluxed in tetradecane as to afford after column chromatography (DCM) the title compound (60%) as an off-white solid.

Intermediate 61

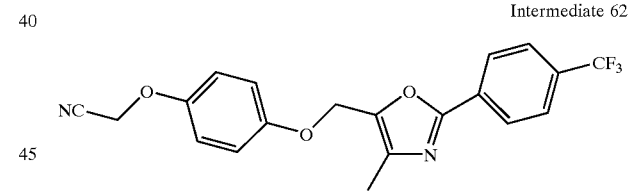

A solution of intermediate 59 (1 g, 4.5 mmol) and NaOH (0.2 g, 5 mmol) in dry MeOH (20 mL) was heated at 70° C. for 5 h. Then, intermediate 5 (1.25 g, 4.5 mmol) was added and the reaction was stirred at 70° C. for one more hour and 18 hours at room temperature. After evaporation of the solvent, the residue was purified by flash column chromatography (DCM) to afford the title compound (71%) as a yellow oil.

Intermediate 62

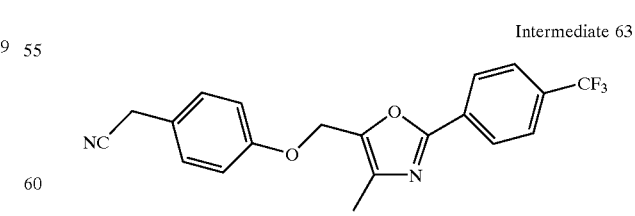

Intermediate 4 and 4-hydroxyphenylacetonitrile were coupled as described in the general procedure 1 to afford the title compound (56%) as a yellow oil.

Intermediate 63

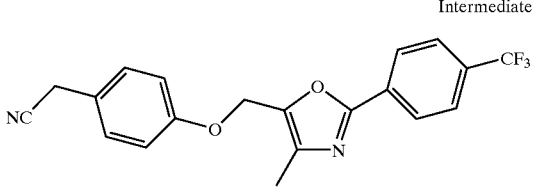

Intermediate 4 and 4-hydroxybenzyl cyanide were coupled as described in the general procedure 1 to afford the title compound (39%) as a pale yellow solid.

Intermediate 64

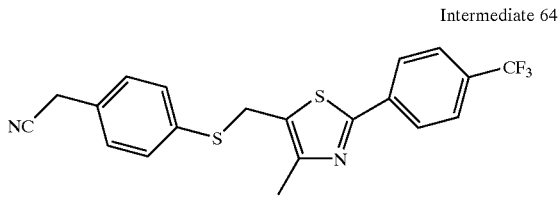

A solution of intermediate 59 (1 g, 4.5 mmol) and NaOH (0.2 g, 5 mmol) in dry MeOH (20 mL) was heated at 70° C. for 5 h. Then, intermediate 2 (1.65 g, 4.5 mmol) was added and the reaction was stirred at 70° C. for one more hour and 18 hours at room temperature. After evaporation of the solvent, the residue was purified by flash column chromatography (DCM) to afford the title compound (75%) as a yellow oil.

Intermediate 65

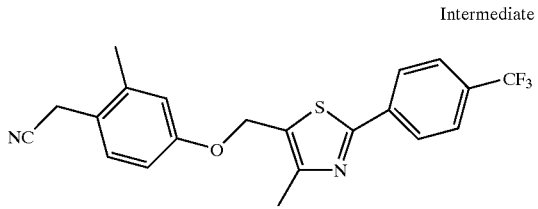

Intermediate 2 and 4-hydroxy-2-methylbenzyl cyanide were coupled as described in the general procedure 1 to afford the title compound (26%) as a white yellow solid.

Intermediate 66

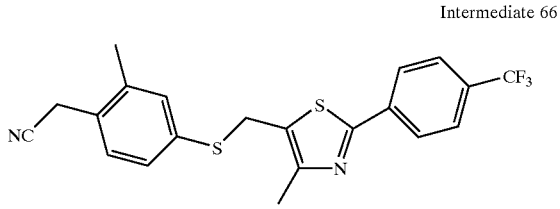

A solution of intermediate 60 (1.67 g, 7.1 mmol) and NaOH (0.32 g, 7.8 mmol) in dry MeOH (20 mL) was heated at 85° C. for 5 h. Then, intermediate 2 (1.65 g, 4.5 mmol) was added and the reaction was stirred at 85° C. for one more hour and 18 hours at room temperature. After evaporation of the solvent, the residue was purified by flash column chromatography (DCM) to afford the title compound (20%) as a yellow oil.

EXAMPLES

General Procedure #1 for the Mitsunobu Coupling of Compounds of Structure A with B To a well stirred solution of A (where X=O) (1.0 mmol), B (0.8 mmol) and $PPh_3$ (262 mg, 1.0 mmol) in dry THF (8.0 mL) at 0° C., was slowly added Diethylazodicaroxylate (DEAD) (174 mg, 157 μl, 1.0 mmol). The reaction was then stirred 48 h at room temperature. After evaporation the crude mixture was purified by flash column chromatography to afford the desired product.

General Procedure #2 for Coupling of A with Alkyl Halides like C

A solution of the A (1.1 mmol), C (1.0 mmol) and $Cs_2CO_3$ (2.2 mmol) in dry acetonitrile (5.0 mL) was stirred overnight at room temperature. The reaction mixture was diluted with $CH_2Cl_2$—(50 mL) and water (50 mL). The organic phase was separated and further washed with 1 N NaOH (2×50 mL), and water (3×50 mL), dried, filtered, and evaporated to afford the final product.

General Procedure #3 for Hydrolysis of Esters.

A solution of the corresponding ester (1 mmol) in THF (1.0 mL) (in some cases few drops of MeOH were added to help solubility), was treated with 1 N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

General Procedure #4 for Heck Coupling Reactions.

A suspension of the corresponding α,β-unsaturated ester (44.0 mmol, 1.75 eq.), the corresponding halophenol (25.0 mmol, 1.0 eq.), $P(o-Tol)_3$ (0.76 g, 2.5 mmol, 0.1 eq.), $Pd_2(dba)_3$ (0.57 g, 0.63 mmol, 0.025 eq.) and $Et_3N$ (2,78 g, 3.83 mL, 27.5 mmol, 1.1 eq.) in dry DMF (10 mL) was stirred overnight at 110° C. (oil bath). After cooling to room temperature, it was partitioned between EtOAc (100 mL) and 2 N HCl (100 mL), filtered through celite, washed with more EtOAc. The organic phase was separated and further washed with water (2×100 mL), dried, filtered and evaporated. The residue was purified by flash column chromatography and/or crystallization.

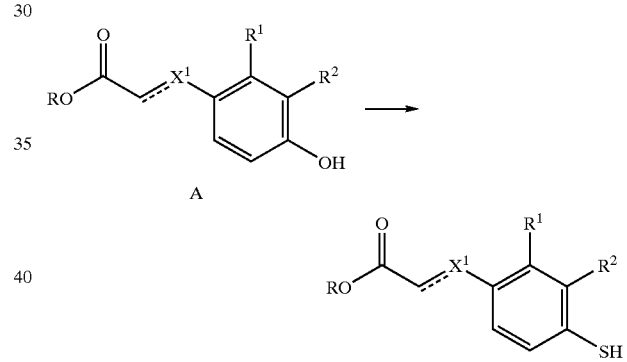

General Procedure #5 for the Conversion of Phenoxyesters to Thiophenoxyesters.

A solution of the corresponding phenoxyacid ester (15 mmol), $Et_3N$ (3.04 g, 4.18 mL, 30 mmol), 4-dimethylamino pyridine (184 mg, 1.5 mmol) and dimethyl thiocarbamoyl chloride (2.22 g, 18 mmol) in dry dioxane (22.5 mL) was refluxed for 16 h. After cooling down to room temp the mixture was partitioned between EtOAc (300 mL) and water (300 mL). The organic layer was separated, washed with water (2×300 mL), dried, filtered and evaporated to afford crude 4-dimethylthiocarbamoyloxy-phenyl ester, that was used in the next step without any further purification.

A suspension of the corresponding crude 4-dimethylthiocarbamoyloxy-phenyl ester (15 mmol) in tetradecane (45 mL) was refluxed for 16 h. After cooling down to room temp., the solvent was decanted and the remaining oil washed several times with hexane. It was purified by flash column chromatography, to afford crude 4-dimethylcarbamoylsulfanyl-phenyl ester.

A solution of the corresponding crude 4-dimethylcarbamoylsulfanyl-phenyl ester (5.0 mmol) in dry MeOH (10 mL) and 0.5 N NaOMe in MeOH (11 mL, 5.5 mmol) was refluxed for 16 h. After cooling down to room temp., the solution was either used without any further purification in the next step or, purified as follows: it was neutralized with 1 N HCl (5.5 mL), and partitioned between EtOAc (200 mL) and water (200 mL). The organic layer was washed with water (2×200 mL), dried, filtered, and evaporated to afford crude material. The mixture was purified by flash column chromatography to afford the thiophenoxy ester.

General Procedure #6 for Coupling 4-dimethylcarbamoylsulfanyl-phenyl Acetonitrile with Alkyl Halides (C)

A solution of the corresponding crude 4-dimethylcarbamoylsulfanyl-phenyl acetonitrile (4.5 mmol) in dry MeOH (10 mL) was added NaOH (0.2 g, 5 mmol).The mixture was refluxed for 5 h. Then the alkyl halide was added and the resulting mixture was refluxed for 1 h and stirred at room temperature for 18 hours. The solvent was removed under reduced pressure and the crude product was purified by flash column chromatography to afford the nitrile derivative.

General Procedure #7 for the Conversion of Nitriles to Tetrazoles.

A mixture of the corresponding nitrile (1.14 g, 3.6 mmol, 1 eq.), dibutyltin oxide (0.36 g, 1.44 mmol, 0.4 eq.) and trimethylsilyl azide (0.53 ml, 3.96 mmol, 1.1 eq.) in toluene (30 mL) was stirred overnight at 150° C. (oil bath) for 4 hours. The solvent was removed under reduced pressure and chased with methanol.

The residue was washed with diethylether to give a solid which was purified by flash column chromatography and/or crystallization to afford the final product.

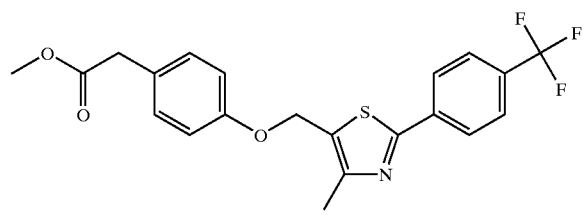

Example 1
methyl 2-[4-({4-methyl-2-[4-(trifluoromethyl)phenyl]-1,3-thiazol-5-yl}methoxy)phenyl]acetate Intermediate 2 and methyl 4-hydroxyphenylacetate were coupled as described in the general procedure 2 to afford the title compound (52%) as a white solid.

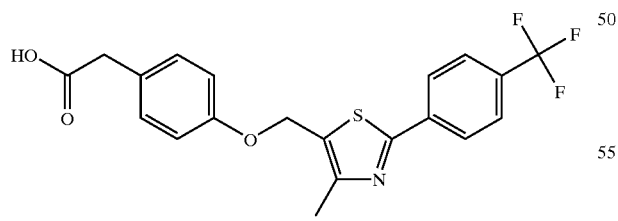

Example 2
2-[4-({4-methyl-2-[4-(trifluoromethyl)phenyl]-1,3-thiazol-5-yl}methoxy)phenyl]acetic acid Example 1 was hydrolyzed as described in the general procedure 3 to afford the title compound (74%) as a solid: mp 149–150° C.

Anal. Calcd. for $C_{20}H_{16}NO_3F_3S$: C, 58.96; H, 3.96; N, 3.44; S, 7.87. Found: C, 58.88; H, 4.04; N, 3.37; S, 7.94.

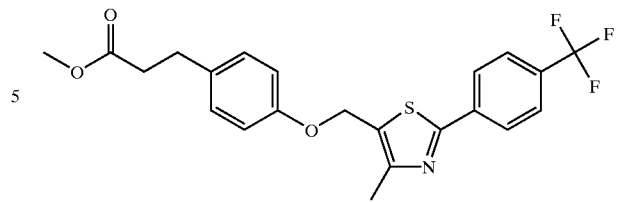

Example 3
methyl 3-[4-({4-methyl-2-[4-(trifluoromethyl)phenyl]-1,3-thiazol-5-yl}methoxy)phenyl]propanoate Intermediate 1 and methyl 3-(4'-hydroxyphenyl)-propanoate were coupled as described in the general procedure 1 to afford the title compound (23%).

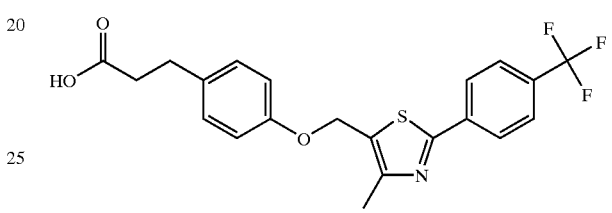

Example 4
3-[4-({4-methyl-2-[4-(trifluoromethyl)phenyl]-1,3-thiazol-5-yl}methoxy)phenyl]propanoic acid Example 3 was hydrolyzed as described in the general procedure 3 to afford the-title compound (72%) as a solid: mp 172–174° C.

Anal. Calcd. for $C_{21}H_{18}NO_3F_3S$: C, 59.85; H, 4.31; N, 3.32. Found: C, 59.79; H, 4.38; N, 3.36.

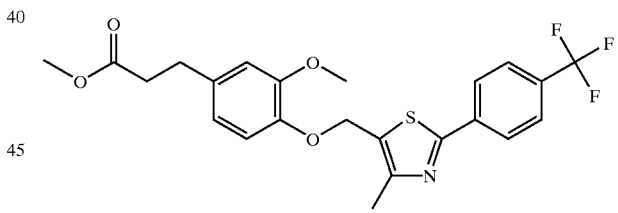

Example 5
methyl 3-[3-methoxy-4-({4-methyl-2-[4-trifluoromethyl)phenyl]-1,3-thiazol-5-yl}methoxy)phenyl]propanoate Intermediate 1 and methyl 3-(3'-methoxy-4'-hydroxyphenyl)-propanoate were coupled as described in the general procedure 1 to afford the title compound (22%).

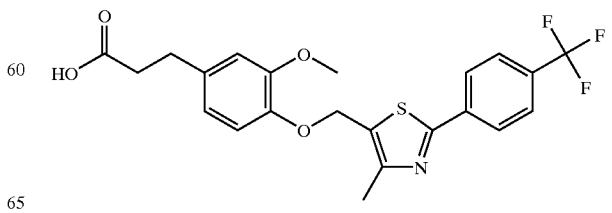

Example 6

3-[3-methoxy-4-({4-methyl-2-[4-trifluoromethyl)phenyl]-1,3-thiazol-5-yl}methoxy)phenyl]propanoic acid Example 5 was hydrolyzed as described in the general procedure 3 to afford the title compound (73%) as a solid: mp 150–152° C.

Anal. Calcd. for $C_{22}H_{20}NO_4F_3S$: C, 58.53; H, 4.47; N, 3.10; S, 7.10. Found: C, 58.31; H, 4.45; N, 3.07; S, 6.98.

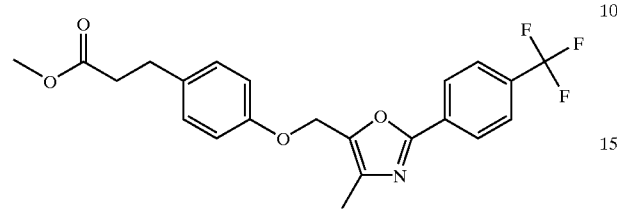

Example 7

Methyl-3-[4-({4-methyl-2-[4-(trifluoromethyl)phenyl]-1,3-oxazol-5-yl}methoxy)phenyl]propanoic acid Intermediate 4 and methyl-3-(4-hydroxyphenyl)-propanoate were coupled as described in the general procedure 1 to afford the title compound (60%) as a yellow solid.

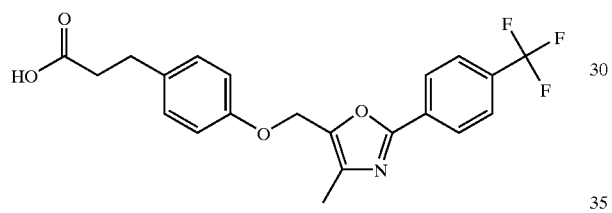

Example 8

3-[4-({4-methyl-2-[4-(trifluoromethyl)phenyl]-1,3-oxazol-5-yl}methoxy)phenyl]propanoic acid Example 7 was hydrolyzed as described in the general procedure 3. The crude material was crystallized from acetone:hexane to afford the title compound (85%) as a white solid: mp 98–100° C.

Anal. Calcd. for $C_{21}H_{18}NO_4F_3$: C, 62.22; H, 4.48; N, 3.46. Found: C, 62.03; H, 4.51; N, 3.46.

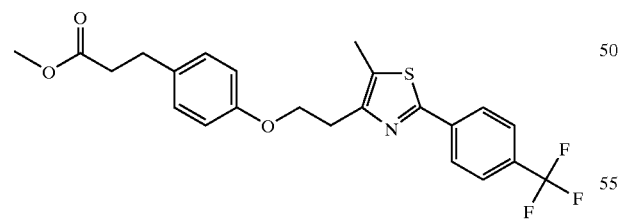

Example 9

Methyl-3-[4-(2-{5-methyl-2-[4-(trifluoromethyl)phenyl]-1,3-thiazol-4-yl}ethoxy)phenyl]propionate Intermediate 13 and methyl 3-(4'-hydroxyphenyl)-propanoate were coupled as described in the general procedure 1 to afford after column chromatography (hexane:EtOAc, 4:1) compound the title compound (20%) as a white solid.

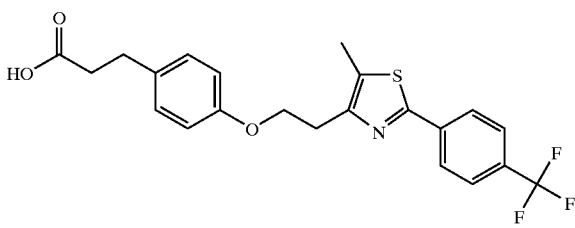

Example 10

3-[4-(2-{5-methyl-2-[4-(trifluoromethyl)phenyl]-1,3-thiazol-4-yl}ethoxy)phenyl]propanoic acid Example 9 was hydrolyzed as described in the general procedure to afford the title compound (45%) as a white solid: mp 142–147° C. HPLC showed one peak at 3.942 min.

Calcd. Mass for $C_{22}H_{20}NO_3F_3S$: $(M+1)^+$: 436.1194. Found (H.R.M.S): 436.1173.

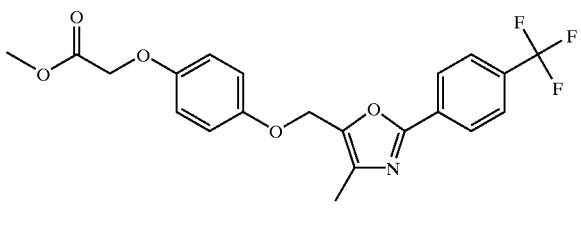

Example 11

Methyl 2-[4-({4-methyl-2-[4-(trifluoromethyl)phenyl]-1,3-oxazol-5-yl}methoxy)phenoxy]acetate Intermediate 4 and methyl 4-hydroxyphenoxyacetate were coupled as described in the general procedure 1 to afford the title compound (33%).

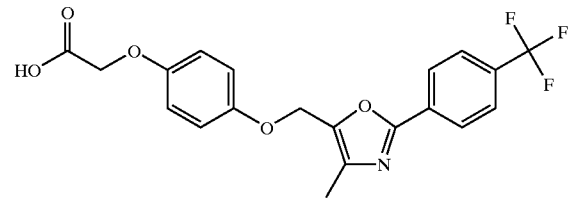

Example 12

2-[4-({4-methyl-2-[4-(trifluoromethyl)phenyl]-1,3-oxazol-5-yl}methoxy)phenoxy]acetic acid Example 11 was hydrolyzed as described in the general procedure 3 to afford the title compound (43%) as a white solid: mp 136–138° C.

Anal. Calcd. for $C_{20}H_{16}NO_5F_3$: C, 58.87; H, 3.96; N, 3.44. Found: C, 58.88; H, 4.00; N, 3.37.

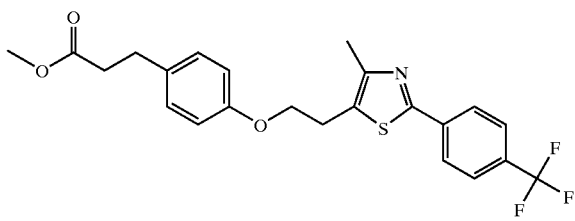

Example 13
Methyl 3-[4-(2-{4-methyl-2-[4-(trifluoromethyl)phenyl]-1,3-thiazol-5-yl}ethoxy)phenyl]propanoate Intermediate 11 and methyl 3-(4'-hydroxyphenyl)-propanoate were coupled as described in the general procedure 1 to afford after flash column chromatography (hexane:EtOAc, 4:1) the title compound (40%) as a white solid.

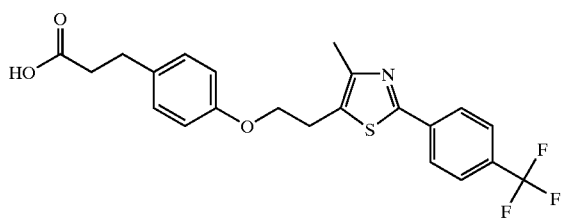

Example 14
3-[4-(2-{4-methyl-2-[4-(trifluoromethyl)phenyl]-1,3-thiazol-5-yl}ethoxy)phenyl]propanoic acid Example 13 was hydrolyzed as described in general procedure 3 to afford the title compound (85%) as a white solid: mp 128–130° C.

Anal. Calcd. for $C_{22}H_{20}NO_3F_3S$: C, 60.68; H, 4.63; N, 3.22; S, 7.36. Found: C, 60.56; H, 4.65; N, 3.22; S, 7.28.

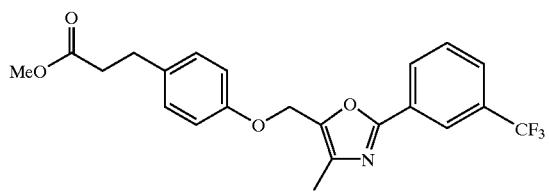

Example 15
Methyl 3-[4-({4-methyl-2-[3-(trifluoromethyl)phenyl]-1,3-oxazol-5-yl}methoxy)phenyl]propanoate Intermediate 7 and 3-(4'-hydroxyphenyl)-propanoate were coupled as described in the general procedure 1 to afford after column chromatography (hexane:AcOEt, 2:1) the title compound (45%) as a colorless oil.

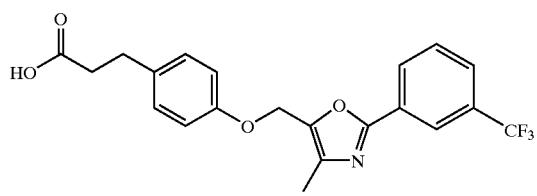

Example 16
3-[4-({4-methyl-2-[3-(trifluoromethyl)phenyl]-1,3-oxazol-5-yl}methoxy)phenyl]propanoic acid Example 15 was hydrolyzed as described in the general procedure 3 to afford the title compound (82%) as a white solid: mp 134–135° C.

Anal. Calcd. for $C_{21}H_{18}NO_4F_3$: C, 62.22; H, 4.48; N, 3.46. Found: C, 62.31; H, 4.55; N, 3.41.

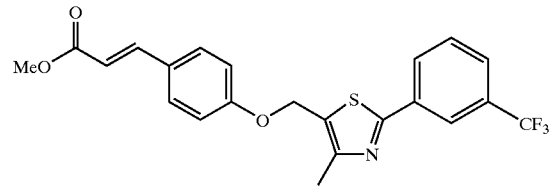

Example 17
Methyl (E)-3-[4-({4-methyl-2-[3-(trifluoromethyl)phenyl]-1,3-thiazol-5-yl}methoxy)phenyl]-2-propenoate Intermediate 2 and methyl 4-hydroxycinnamate were coupled as described in the general procedure 2 to afford the title compound (92%) as a yellow solid.

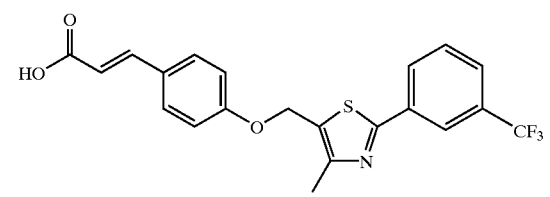

Example 18
(E)-3-[4-({4-methyl-2-[4-(trifluoromethyl)phenyl]-1,3-thiazol-5-yl}methoxy)phenyl]-2-propenoic acid Example 17 was hydrolyzed as described in the general procedure. The crude material was crystallized from acetone:water to afford the title compound (85%) as a white solid: mp 226–228° C.

Anal. Calcd. for $C_{21}H_{16}NO_3F_3S$: C, 60.14; H, 3.85; N, 3.34; S, 7.65. Found: C, 60.07; H, 3.75; N, 3.39; S, 7.65.

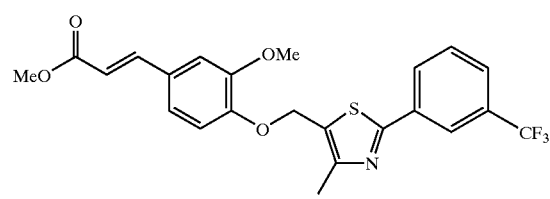

Example 19
Methyl (E)-3-[3-methoxy-4-({4-methyl-2-[3-(trifluoromethyl)phenyl]-1,3-thiazol-5-yl}methoxy)phenyl]-2-propenoate Intermediate 2 and methyl 4-hydroxy-3-methoxycinnamate were coupled as described in the general procedure 2 to afford the title compound (100%) as a yellow solid.

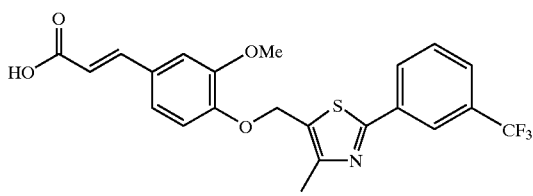

Example 20
(E)-3-[3-methoxy-4-({4-methyl-2-[4-(trifluoromethyl)phenyl]-1,3-thiazol-5-yl}methoxy)phenyl]-2-propenoic acid Example 19 was hydrolyzed as described in general procedure 3. The crude material was crystallized from acetone:water to afford the title compound (62%) as a white solid: mp 235–237° C.

Anal. Calcd. for $C_{22}H_{18}NO_4F_3S$: C, 58.79; H, 4.04; N, 3.12; S, 7.13. Found: C, 59.03; H, 4.09; N, 3.13; S, 7.03.

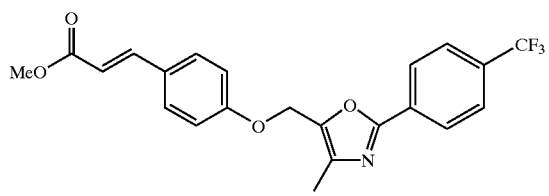

Example 21
Methyl (E)-3-[4-({4-methyl-2-[4-(trifluoromethyl)phenyl]-1,3-oxazol-5-yl}methoxy)phenyl]-2-propenoate Intermediate 5 and methyl 4-hydroxycinnamate were coupled as described in the general procedure 2 to afford the title compound (60%) as a solid.

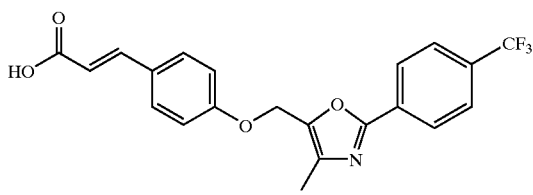

Example 22
(E)-3-[4-({4-methyl-2-[4-(trifluoromethyl)phenyl]-1,3-oxazol-5-yl}methoxy)phenyl]-2-propenoic acid Example 21 was hydrolyzed as described in the general procedure 3 to afford the title compound (92%) as a white solid: mp 193° C. HPLC showed one peak at 3.689 min.

Calcd. Mass for $C_{21}H_{16}NO_4F_3$: $(M+1)^+$: 404.1110. Found (H.R.M.S): 404.1098.

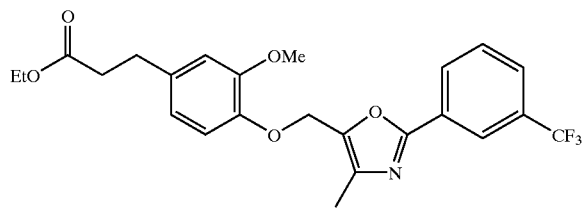

Example 23
Ethyl 3-[3-methoxy-4-({4-methyl-2-[3-trifluoromethyl)phenyl]-1,3-oxazol-5-yl}methoxy)phenyl]propanoate Intermediate 5 and ethyl 3-(4-hydroxy-3-methoxyphenyl)propanoate were coupled as described in the general procedure 2 to afford the title compound (89%) as an oil.

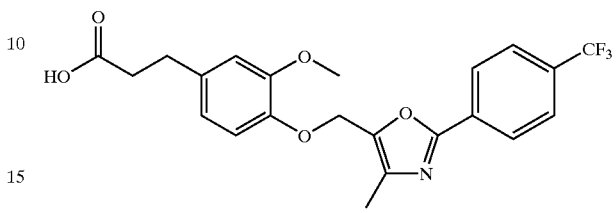

Example 24
3-[3-methoxy-4-({4-methyl-2-[4-(trifluoromethyl)phenyl]-1,3-oxazol-5-yl}methoxy)phenyl]propanoic acid Example 23 was hydrolyzed as described in general procedure 3 to afford the title compound (67%) as a solid: mp 162–163° C.

Anal. Calcd. for $C_{22}H_{20}NO_5F_3$: C, 60.69; H, 4.63; N, 3.22. Found: C, 60.52; H, 4.71; N, 3.21.

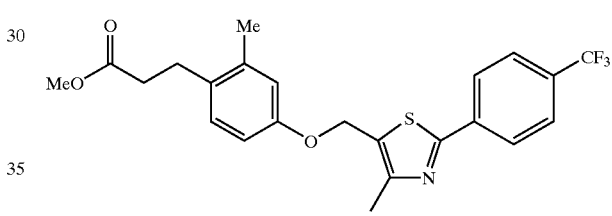

Example 25
Methyl 3-[2-methyl-4-({4-methyl-2-[4-trifluoromethyl)phenyl]-1,3-thiazol-5-yl}methoxy)phenyl]propanoate Intermediate 2 and intermediate 15 were coupled as described in the general procedure 2 to afford the title compound (94%) as a brown solid.

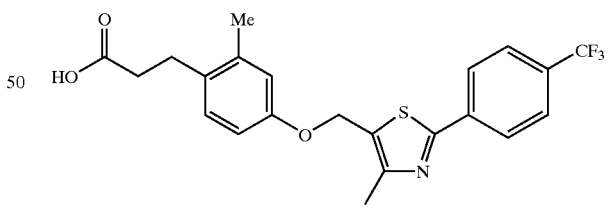

Example 26
3-[2-methyl-4-({4-methyl-2-[4-(trifluoromethyl)phenyl]-1,3-thiazol-5-yl}methoxy)phenyl]propanoic acid Example 25 was hydrolyzed as described in general procedure 3. The crude material was crystallized from EtOAc:hexane to afford the title compound (40%) as yellow solid: mp 141–143° C.

Anal. Calcd. for $C_{22}H_{20}NO_3F_3S$: C, 60.68; H, 4.63; N, 3.22; S, 7.36. Found: C, 60.44; H, 4.78; N, 3.17; S, 7.25.

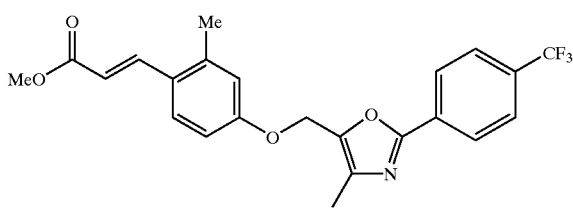

Example 27
Methyl (E)-3-[2-methyl-4-({4-methyl-2-[4-(trifluoromethyl)phenyl]-1,3-oxazol-5-yl}methoxy)phenyl]-2-propenoate Intermediate 5 and intermediate 14 were coupled as described in the general procedure 2 to afford the title compound as a white solid: mp 124–126° C. (72%).

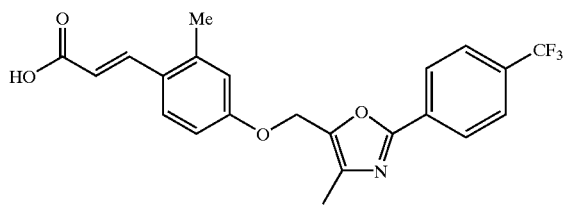

Example 28
(E)-3-[2-methyl-4-({4-methyl-2-[4-(trifluoromethyl)phenyl]-1,3-oxazol-5-yl}methoxy)phenyl]-2-propenoic acid Example 27 was hydrolyzed as described in the general procedure to afford the title compound (97%) as white solid: mp 155–165° C. HPLC showed one peak at 3.579 min.

Calcd. Mass for $C_{22}H_{18}NO_4F_3$: $(M+1)^+$: 418.1266. Found (H.R.M.S): 418.1278.

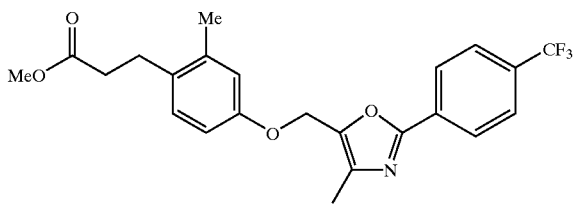

Example 29
Methyl 3-[2-methyl-4-({4-methyl-2-[4-(trifluoromethyl)phenyl]-1,3-oxazol-5-yl}methoxy)phenyl]propanoate Intermediate 5 and intermediate 15 were coupled as described in the general procedure 2 to afford the title compound (80%) as an oil.

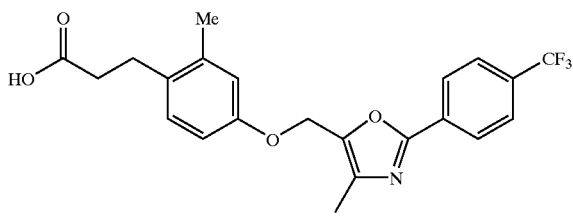

Example 30
3-[2-methyl-4-({4-methyl-2-[4-(trifluoromethyl)phenyl]-1,3-oxazol-5-yl}methoxy)phenyl]propanoic acid Example 29 was hydrolyzed as described in the general procedure 3. The crude material was crystallized from acetone:hexane to afford the title compound (50%) as yellow solid: mp 113–115° C.

Anal. Calcd. for $C_{22}H_{20}NO_4F_3$: C, 63.00; H, 4.81; N, 3.34. Found: C, 63.07; H, 4.83; N, 3.43.

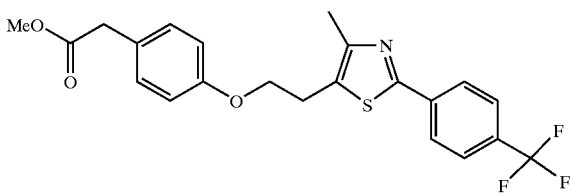

Example 31
Methyl 2-[4-(2-{4-methyl-2-[4-trifluoromethyl)phenyl]-1,3-thiazol-5-yl}ethoxy)phenyl]acetate Intermediate 11 and methyl 4-hydroxylphenylacetate were coupled as described in the general procedure 1 to afford after flash column chromatography (hexane: EtOAc, 4:1) compound the title compound (42%) as a white solid.

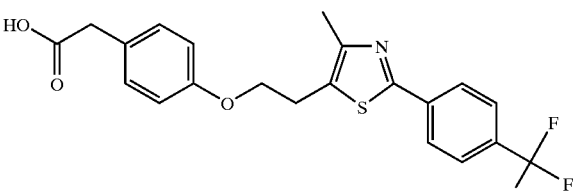

Example 32
2-[4-(2-{4-methyl-2-[4-(trifluoromethyl)phenyl]-1,3-thiazol-5-yl}ethoxy)phenyl]acetic acid Example 31 was hydrolyzed as described in general procedure 3. The crude material was crystallized from acetone:water to afford the title compound (97%) as a white solid: mp 128–130° C.

Anal. Calcd. for $C_{21}H_{18}NO_3F_3S$: C, 59.85; H, 4.31; N, 3.32; S, 7.61. Found: C, 59.92; H, 4.41; N, 3.26; S, 7.52.

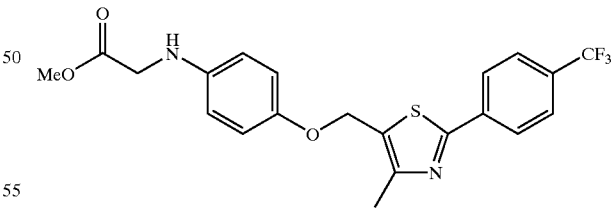

Example 33
Methyl-N-[4-(2-[4-trifluromethylphenyl]-4-methyl-thiazol-5-ylmethoxy)anilino]-acetate Methyl N-(4-hydroxyphenyl)glycinate and intermediate 2 were coupled as described in general procedure 2 to afford the title compound (25%) as a yellow solid.

$^1$H-NMR (acetone-d6) δ2.32(s, 3H), 3.53(s, 3H), 3.75 (s, 2H), 5.08 (s, 2H), 6.43(d, 2H), 6.72(d, 2H), 7.68 (d, 2H), 8.02(d, 2H). MS m/z 437 (M+1)

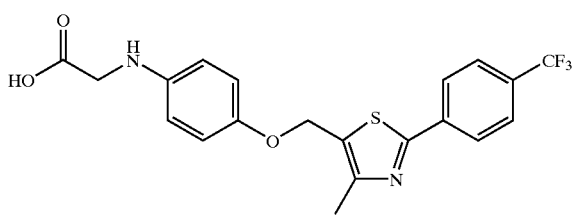

Example 34
2-[4-({4-methyl-2-[4-(trifluoromethyl)phenyl]-1,3-thiazol-5-yl}methoxy)anilino]acetic acid Example 33 was hydrolyzed as described in the general procedure 3 to afford the title compound (20%) as a yellow solid.

$^1$H-NMR (acetone-d6) δ2.47 (s, 3H), 3.89(s, 2H), 5.09 (s, 2H),6.51(d, 2H), 6.73 (d, 2H), 7.83 (d, 2H), 8.06(d,2H). MS m/z 437(M+1)-.

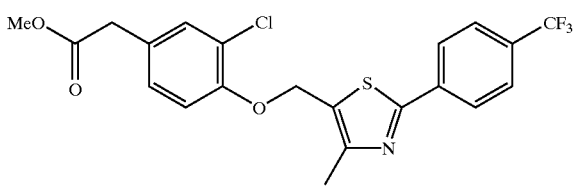

Example 35
methyl 2-[3-chloro-4-({4-methyl-2-[4-(trifluoromethyl)phenyl]-1,3-thiazol-5-yl}methoxy)phenyl]acetate Intermediate 2 and methyl-3-chloro-4-hydroxy phenylacetate were coupled as described in general procedure 2 to afford the title compound (70%) as a yellow solid.

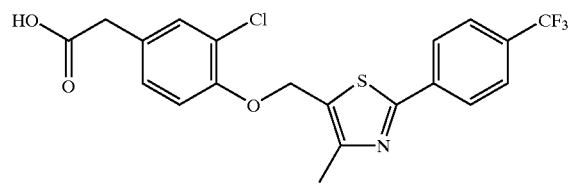

Example 36
2-[3-chloro-4-({4-methyl-2-[4-(trifluoromethyl)phenyl]-1,3-thiazol-5-yl}methoxy)phenyl]acetic acid Example 35 was hydrolyzed as described in general procedure 3 to afford the title compound (90%) as a white solid: mp 126–127° C.

Anal. Calcd. for $C_{20}H_{15}NO_3F_3SCl$: C, 54.37; H, 3.42; N, 3.17. Found: C, 54.41; H, 3.41; N, 3.24.

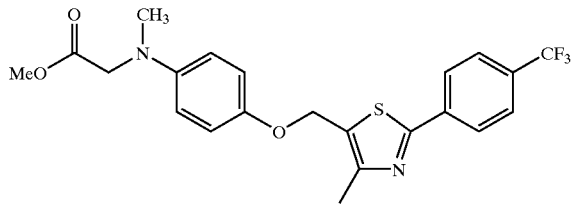

Example 37
Methyl-N-methyl-N-[4-(2-[4-trifluromethylphenyl]-4-methyl-thiazol-5-ylmethoxy)anilino]-acetate Intermediate 17 and intermediate 2 were coupled as described in general procedure 2 to afford the title compound (35%) as a yellow solid: 1H-NMR (acetone-d6) δ2.46(s, 3H), 3.01(s, 3H), 3.64 (s, 3H), 4.10 (s,3H), 5.25(s, 2H), 6.80(d, 2H), 6.92 (d,2H),7.82(d, 2H),8.18 (d,2H).

MS m/z 451 (M+1)

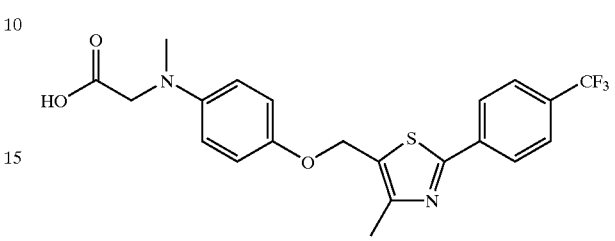

Example 38
N-Methyl-N-[4-(2-[4-trifluromethylphenyl]-4-methyl-thiazole-5-ylmethoxy)phenyl]-acetic acid Example 37 was hydrolyzed as described in general procedure 3 to afford the title compound (45%) as a yellow solid: mp 124–126° C.; 1H-NMR (acetone-d6) δ2.47 (s, 3H), 3.09(s, 3H), 408(s, 2H),5.25 (s, 2H), 6.70(d, 2H), 6.91(d, 2H), 7.83 (d, 2H), 8.16(d,2H); MS m/z 437(M+1)-. This compound was unstable and gradually decomposed at ambient temperature.

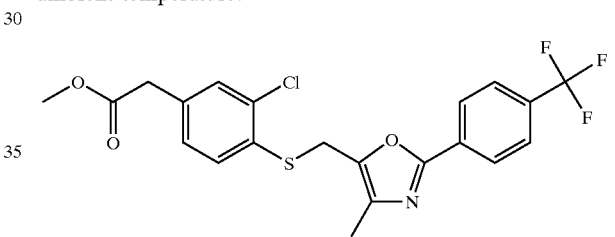

Example 39
methyl 2-{3-chloro-4-[({4-methyl-2-[4-(trifluoromethyl)phenyl]-1,3-oxazol-5-yl}methyl)sulfanyl]phenyl}acetate A solution of intermediate 18 (200 mg, 0.8 mmol) in dry MeOH (2 mL) and 0.5N NaOMe in MeOH (1.6 mL, 0.8 mmol) was heated at 70° C. for 3 h. Then, intermediate 5 (184 mg, 0.63 mmol) was added and the reaction was stirred at 70° C. for one more hour. After evaporation of the solvent, the residue was purified by flash column chromatography (hexane:EtOAc, 9:1) to afford the title compound (34%) as a yellow solid.

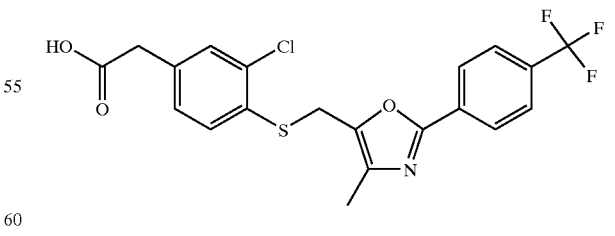

Example 40
2-{3-chloro-4-[({4-methyl-2-[4-trifluoromethyl)phenyl]-1,3-oxazol-5-yl}methyl)sulfanyl]phenyl}acetic acid Example 39 was hydrolyzed as described in general procedure 3 to afford the title compound (46%) as white solid: mp 158–160° C.

Anal. Calcd. for $C_{20}H_{15}NO_3F_3SCl \cdot 0.20$ HCl: C, 53.48; H, 3.42; N, 3.12; S, 7.20. Found: C, 53.55; H, 3.42; N, 3.08; S, 7.17.

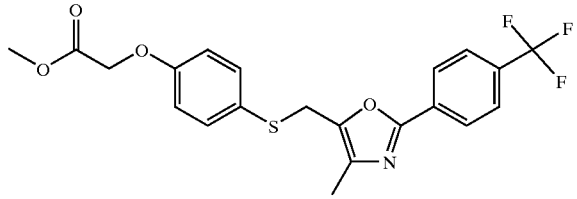

Example 41 methyl 2-[4-({4-methyl-2-[4-(trifluoromethyl)phenyl]-1,3-oxazol-5-yl}methyl)sulfanyl]phenoxy}acetate A solution of intermediate 19 (200 mg, 0.8 mmol) in dry MeOH (2 mL) and 0.5 N NaOMe in MeOH (1.6 mL, 0.8 mmol) was heated at 70° C. for 3 h. Then, intermediate 5 (184 mg, 0.63 mmol) was added and the reaction was stirred at 70° C. for one more hour. After evaporation of the solvent, the residue was purified by flash column chromatography (hexane:EtOAc, (9:1) to afford the title compound (14%) as a yellow solid.

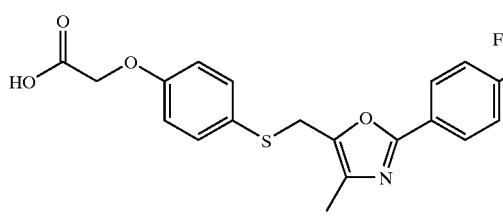

Example 42

2-[4-[({4-methyl-2-[4-trifluoromethyl)phenyl]-1,3-oxazol-5-yl}methyl)sulfanyl]phenoxy}acetic acid Example 41 was hydrolyzed as described in general procedure 3 to afford the title compound (68%) as yellow solid: mp 131–133° C.

Anal. Calcd. for $C_{20}H_{16}NO_4F_3S$: C, 56.73; H, 3.81; N, 3.31. Found: C, 57.03; H, 4.05; N, 3.28.

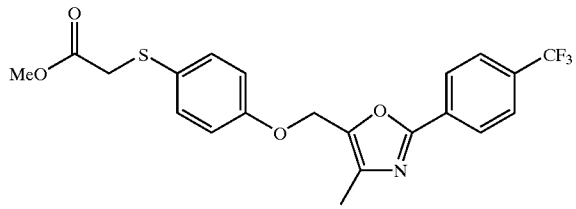

Example 43

Methyl 2-{[4-({4-methyl-2-[4-(trifluoromethyl)phenyl]-1,3-oxazol-5-yl}methoxy)phenyl]sulfanyl}acetate Intermediate 5 and methyl 2-(4-hydroxyphenylthio) acetate were coupled as described in the general procedure 2 to afford the title compound (69%) as an oil.

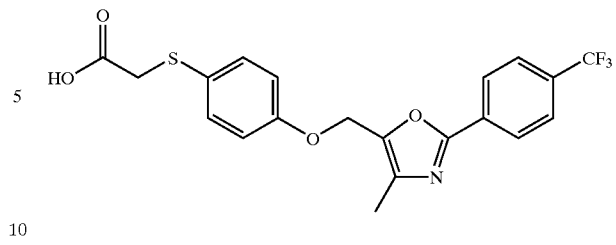

Example 44

2-{[4-({4-methyl-2-[4-trifluoromethyl)phenyl]-1,3-oxazol-5-yl}methoxy)phenyl]sulfanyl}acetic acid Example 43 was hydrolyzed as described in general procedure 3 to give crude material, that was purified by flash column chromatography (CHCl$_3$:MeOH, 9:1) and then crystallized from ether to afford the title compound (50%) as a white solid: mp 138–140° C. HPLC showed one peak at 3.580 min.

Calcd. Mass for $C_{20}H_{16}NO_4F_3S$: $(M+1)^+$: 424.0830. Found (H.R.M.S): 424.0821.

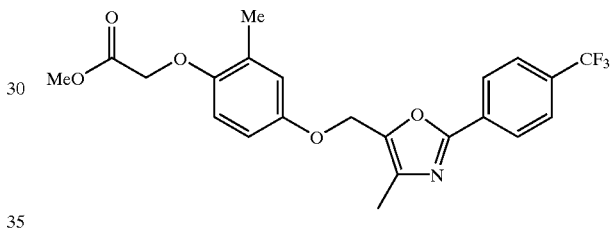

Example 45

Methyl 2-[2-methyl-4-({4-methyl-2-[4-trifluoromethyl)phenyl]-1,3-oxazol-5-yl}methoxy)phenoxy]acetate Intermediate 5 and intermediate 22 were coupled as described in general procedure 1 to afford the title compound (70%) as a brown solid.

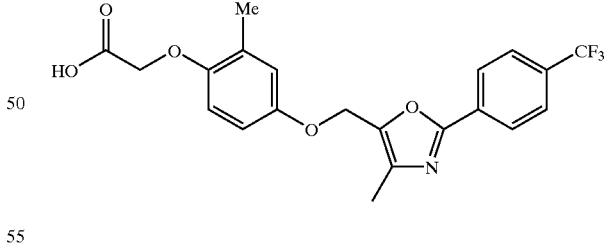

Example 46

2-[2-methyl-4-({4-methyl-2-[4-(trifluoromethyl)phenyl]-1,3-oxazol-5-yl}methoxy)phenoxy]acetic acid Example 45 was hydrolyzed as described in general procedure 3. The crude material was crystallized from MeOH:water to afford the title compound (90%) as a yellow solid: mp 136–137° C.

Anal. Calcd. for $C_{21}H_{18}NO_5F_3$: C, 59.86; H, 4.31; N, 3.32. Found: C, 59.77; H, 4.45; N, 3.32.)

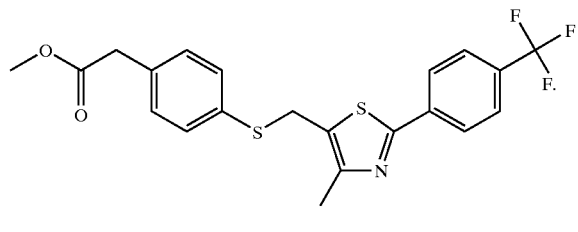

Example 47 methyl 2-{4-[({4-methyl-2-[4-(trifluoromethyl)phenyl]-1,3-thiazol-5-yl}methyl)sulfanyl]phenyl}acetate A solution of intermediate 23 (200 mg, 0.8 mmol) in dry MeOH (2 mL) and 0.5N NaOMe in MeOH (1.6 mL, 0.8 mmol) was heated at 70° C. for 3 h. Then, intermediate 2 (184 mg, 0.63 mmol) was added and the reaction was stirred at 70° C. for one more hour. After evaporation of the solvent, the residue was purified by flash column chromatography (hexane:EtOAc, 9:1) to afford the title compound (36%) as a yellow solid.

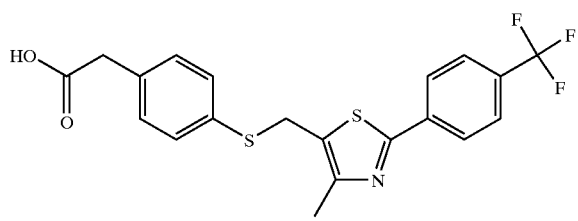

Example 48

2-{4-[({4-methyl-2-[4-(trifluoromethyl)phenyl]-1,3-thiazol-5-yl}methyl)sulfanyl]phenyl}acetic acid Example 47 was hydrolyzed as described in general procedure 3 to afford the title compound (78%) as white solid: mp 202–203° C.

Anal. Calcd. for $C_{20}H_{16}NO_2F_3S_2$ 0.85 HCl: C, 52.86; H, 3.74; N, 3.08. Found: C, 52.85; H, 3.93; N, 3.11.

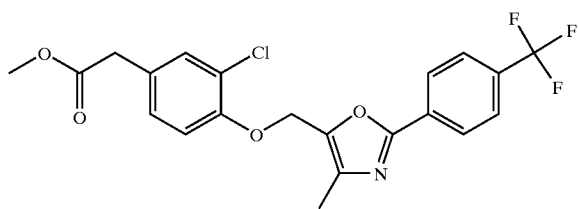

Example 49 methyl 2-[3-chloro-4-({4-methyl-2-[4-(trifluoromethyl)phenyl]-1,3-oxazol-5-yl}methoxy)phenyl]acetate Intermediate 5 and methyl-3-chloro-4-hydroxyphenylacetate were coupled as described in general procedure 2 to afford the title compound (65%) as a yellow solid.

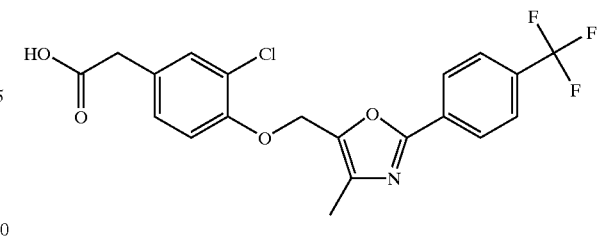

Example 50

2-[3-chloro-4-({4-methyl-2-[4-(trifluoromethyl)phenyl]-1,3-oxazol-5-yl}methoxy)phenyl]acetic acid Example 49 was hydrolyzed as described in general procedure 3 to afford the title compound (73%) as a white solid: mp 189–191° C.

Anal. Calcd. for $C_{20}H_{15}NO_4F_3Cl$ 1.0 HCl: C, 51.96; H, 3.49; N, 3.03. Found: C, 51.67; H, 3.65; N, 3.03.

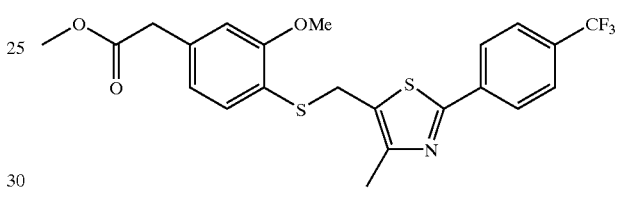

Example 51 methyl 2-{3-methoxy-4-[({4-methyl-2-[4-(trifluoromethyl)phenyl]-1,3-thiazol-5-yl}methyl)sulfanyl]phenyl}acetate A solution of intermediate 24 (200 mg, 0.8 mmol) in dry MeOH (2 mL) and 0.5 N NaOMe in MeOH (1.6 mL, 0.8 mmol) was heated at 70° C. for 3 h. Then, intermediate 2 (184 mg, 0.63 mmol) was added and the reaction was stirred at 70° C. for one more hour. After evaporation of the solvent, the residue was purified by flash column chromatography (hexane:EtOAc, 4:1) to afford the title compound (32%) as a yellow solid.

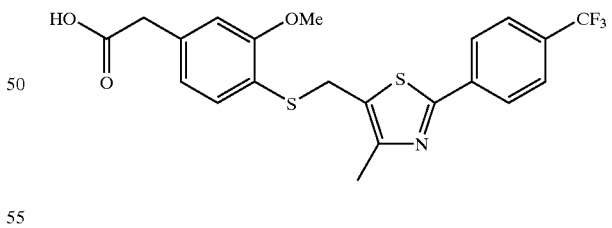

Example 52

2-{3-methoxy-4-[({4-methyl-2-[4-(trifluoromethyl)phenyl]-1,3-thiazol-5-yl}methyl)sulfanyl]phenyl}acetic acid Example 51 was hydrolyzed as described in general procedure 3 to afford the title compound (21%) as white solid: mp 181–182° C.

Anal. Calcd. for $C_{21}H_{18}NO_3F_3S_2$ 0.25 HCl: C, 54.52; H, 3.98; N, 3.03. Found: C, 54.53; H, 4.23; N, 2.79.

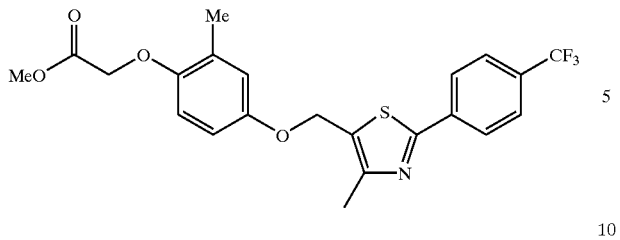

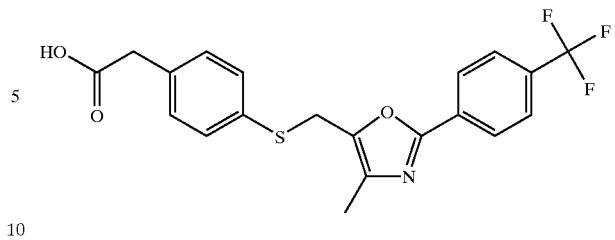

Example 53

Methyl 2-[2-methyl-4-({4-methyl-2-[4-(trifluoromethyl)phenyl]-1,3-thiazol-5-yl}methoxy)phenoxy]acetate Intermediate 2 and intermediate 22 were coupled as described in the general procedure 2 to afford the title compound (74%) as a yellow solid.

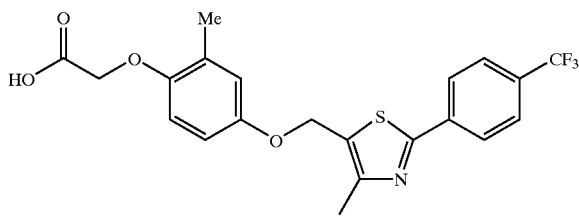

Example 54

2-[2-methyl-4-({4-methyl-2-[4-(trifluoromethyl)phenyl]-1,3-thiazol-5-yl}methoxy)phenoxy]acetic acid Example 53 was hydrolyzed as described in general procedure 3 to afford the title compound (64%) as a yellow solid: mp 174–176° C.

Anal. Calcd. for $C_{21}H_{18}NO_4F_3S$: C, 57.66; H, 4.15; N, 3.20; S, 7.33. Found: C, 57.67; H, 4.18; N, 3.15; S, 7.30.

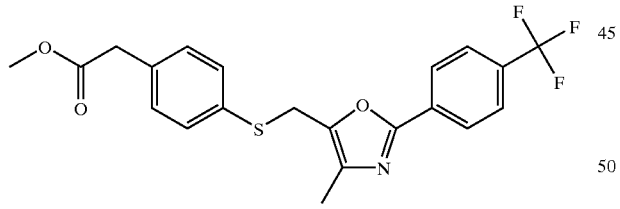

Example 55 methyl 2-{4-[({4-methyl-2-[4-(trifluoromethyl)phenyl]-1,3-oxazol-5-yl}methyl)sulfanyl]phenyl}acetate A solution of intermediate 23 (200 mg, 0.8 mmol) in dry MeOH (2 mL) and 0.5N NaOMe in MeOH (1.6 mL, 0.8 mmol) was heated at 70° C. for 3 h. Then, intermediate 5 (184 mg, 0.63 mmol) was added and the reaction was stirred at 70° C. for one more hour. After evaporation of the solvent, the residue was purified by flash column chromatography (hexane:EtOAc, 4:1) to afford the title compound (10%) as a yellow solid.

Example 56

2-{4-[({4-methyl-2-[4-(trifluoromethyl)phenyl]-1,3-oxazol-5-yl}methyl)sulfanyl]phenyl}acetic acid Example 55 was hydrolyzed as described in general procedure 3 to afford the title compound (92%) as white solid: mp 135–136° C.

Anal. Calcd. for $C_{20}H_{16}NO_3F_3S$ 0.50 HCl: C, 56.44; H, 3.91; N, 3.29. Found: C, 56.14; H, 3.85; N, 3.10.

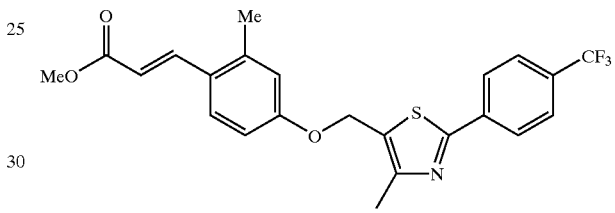

Example 57

Methyl (E)-3-[2-methyl-4-({4-methyl-2-[4-trifluoromethyl)phenyl]-1,3-thiazol-5-yl}methoxy)phenyl]-2-propenoate Intermediate 2 and intermediate 14 were coupled as described in the general procedure 2 to afford the title compound (100%) as a brown solid.

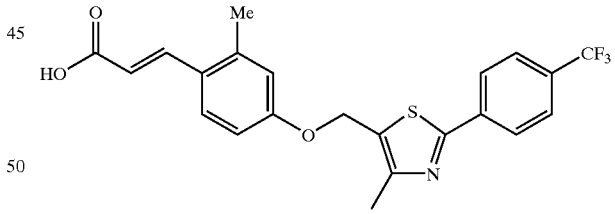

Example 58

(E)4-[2-methyl-4-({4-methyl-2-[4-(trifluoromethyl)phenyl]-1,3-thiazol-5-yl}methoxy)phenyl]-2-propenoic acid Example 57 was hydrolyzed as described in general procedure 3. The crude material was crystallized from EtOAc:hexane to afford the title compound (25%) as a white solid: mp 200–203° C.

Anal. Calcd. for $C_{22}H_{18}NO_3F_3S$: C, 60.96; H, 4.19; N, 3.23. Found: C, 60.74; H, 4.23; N, 3.20.

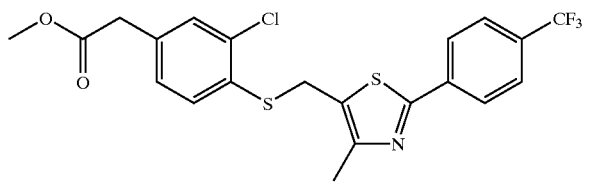

Example 59 methyl 2-{3-chloro-4-[({4-methyl-2-[4-(trifluoromethyl)phenyl]-1,3-thiazol-5-yl}methyl)sulfanyl]phenyl}acetate A solution of intermediate 18 (200 mg, 0.8 mmol) in dry MeOH (2 mL) and 0.5N NaOMe in MeOH (1.6 mL, 0.8 mmol) was heated at 70° C. for 3 h. Then, intermediate 2 (184 mg, 0.63 mmol) was added and the reaction was stirred at 70° C. for one more hour. After evaporation of the solvent, the residue was purified by flash column chromatography (hexane:EtOAc, 9:1) to the title compound (54%) as a yellow solid.

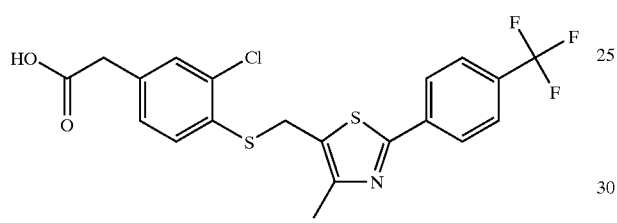

Example 60

2-{3-chloro-4-[({4-methyl-2-[4-(trifluoromethyl)phenyl]-1,3-thiazol-5-yl}methyl)sulfanyl]phenyl}acetic acid Example 59 was hydrolyzed as described in the general procedure. The crude material was crystallized from acetone:hexane to afford the title compound (96%) as white solid:

Anal. Calcd. for $C_{20}H_{15}NO_2F_3S_2Cl$: C, 52.46; H, 3.30; N, 3.06; Cl, 7.74; S, 14.01. Found: C, 52.44; H, 3.35; N, 3.01; Cl, 7.83; S, 13.88.

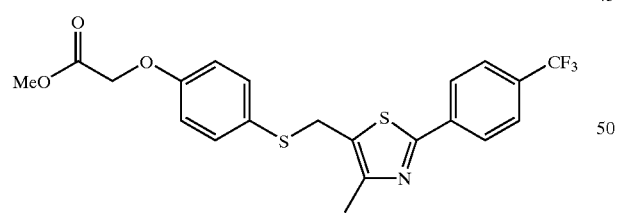

Example 61 methyl 2-{4-[({4-methyl-2-[4-(trifluoromethyl)phenyl]-1,3-thiazol-5-yl}methyl)sulfanyl]phenoxy}acetate A solution of intermediate 19 (200 mg, 0.8 mmol) in dry MeOH (2 mL) and 0.5N NaOMe in MeOH (1.6 mL, 0.8 mmol) was heated at 70° C. for 3 h. Then, intermediate 2 (184 mg, 0.63 mmol) was added and the reaction was stirred at 70° C. for one more hour. After evaporation of the solvent, the residue was purified by flash column chromatography (hexane:EtOAc, 4:1) to afford the title compound (15%) as a yellow solid.

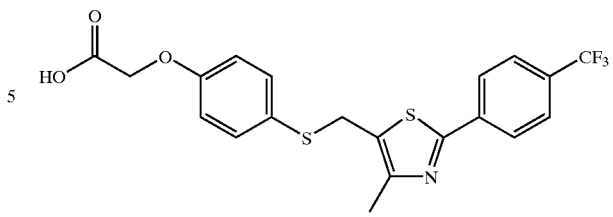

Example 62

2-{4-[({4-methyl-2-[4-(trifluoromethyl)phenyl]-1,3-thiazol-5-yl}methyl)sulfanyl]phenoxy}acetic acid Example 61 was hydrolyzed as described in general procedure 3. The crude material was crystallized from acetone:hexane to afford the title compound (50%) as yellow solid: mp 190° C.

Anal. Calcd. for $C_{20}H_{16}NO_3F_3S_2$: C, 54.66; H, 3.67; N, 3.19; S, 14.59. Found: C, 54.45; H, 3.71; N, 3.02; S, 14.83.

Example 63

Methyl 2-(2-methyl-4-[({4-methyl-2-[4-(trifluoramethyl)phenyl]-1,3-oxazol-5-yl}methyl)sulfanyl]phenoxy}acetate Intermediate 5 and intermediate 25 were coupled as described in general procedure 2 to afford the title compound (85%) as brown solid.

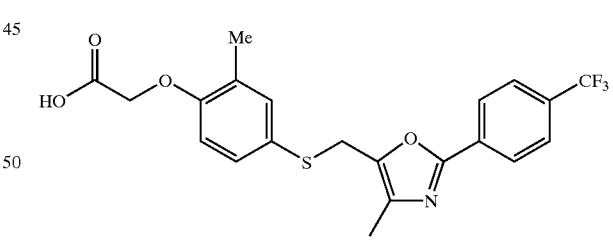

Example 64

2-{2-methyl-4-[({4-methyl-2-[4-(trifluoromethyl)phenyl]-1,3-oxazol-5-yl}methyl)sulfanyl]phenoxy}acetic acid Example 63 was hydrolyzed as described in general procedure 3. The crude material was crystallized from MeOH:water to afford the title compound (67%) as white solid: mp 156–157° C.

Anal. Calcd. for $C_{21}H_{18}NO_4F_3S$: C, 57.66; H, 4.15; N, 3.20; S, 7.33. Found: C, 57.47; H, 4.14; N, 3.13; S, 7.26.

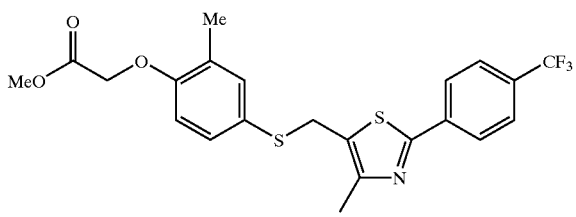

Example 65
Methyl 2-{2-methyl-4-[({4-methyl-2-[4-(trifluoromethyl)phenyl]-1,3-thiazol-5-yl}methyl)sulfanyl]phenoxy}acetate Intermediate 2 and intermediate 25 were coupled as described in general procedure 2 to afford the title compound (87%) as brown solid.

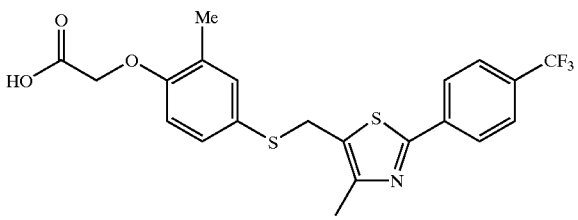

Example 66
2-{2-methyl-4-[({4-methyl-2-[4-(trifluoromethyl)phenyl]-1,3-thiazol-5-yl}methyl)sulfanyl]phenoxy}acetic acid Example 65 was hydrolyzed as described in general procedure 3. The crude material was crystallized from MeOH:water to afford the title compound (60%) as yellow solid: mp 139–141° C.

Anal. Calcd. for $C_{21}H_{18}NO_3F_3S_2$: C, 55.62; H, 4.00; N, 3.09; S, 14.14. Found: C, 55.52; H, 4.11; N. 3.13; S, 14.29.

Alternative preparation of Example 66

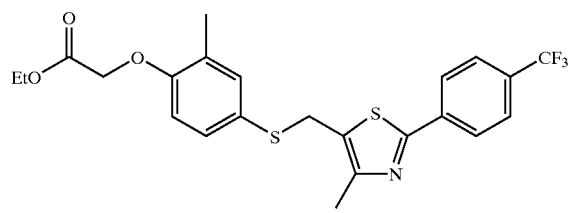

Example 67
2-{2-methyl-4-[({4-methyl-2-[4-(trifluoromethyl)phenyl]-1,3-thiazol-5-yl}methyl)sulfanyl]phenoxy}acetic acid Intermediate 54 (4.68 g, 16 mM) was refluxed with 9.6 g of tin powder in ethanol (20 mL) and dioxane/HCl (20 mL). After 3 h the reaction mixture was poured into ice and $CH_2Cl_2$ (200 mL) and filtered. The phases were separated and the aqueous layer was extracted 2×50 mL $CH_2Cl_2$. The combined organic layers were dried ($MgSO_4$), filtered and evaporated to yield 3.5 g (97%). This material readily forms disulfides and therefore was used immediately. It was dissolved in acetonitrile (50 mL) with intermediate 2 (4.0 g, 14.0 mM) and $Cs_2CO_3$ (10.1 g, 31.0 mM) and stirred for 1 h then diluted with ether (200 mL) and water (200 mL). The phases were separated and the organic phase was washed 2× NaOH 0.1N (50 mL), dried ($MgSO_4$), filtered and evaporated to afford crude product (6.57 g,) which was slurried in hexane:ether (1:1) and filtered to yield the title compound (5.0 g, 74%). This material could be hydrolyzed as above (to yield example 66).

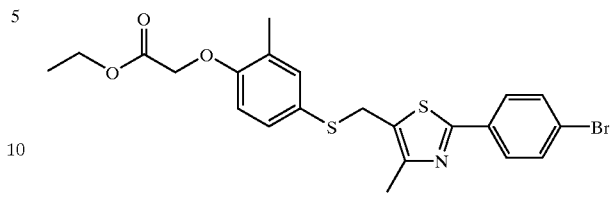

Example 68
ethyl 2-{2-methyl-4-[({4-methyl-2-[4-bromophenyl]-1,3-thiazol-5-yl}methyl)sulfanyl]phenoxy}acetate Intermediate 47 and intermediate 54 were coupled as described for example 67. The crude material was chromatographed cyclohexane/EtOAc (85:15) to afford the title compound (61%) as a clear oil.

1H-NMR (CDCl3) δ1.45 (t, 3H), 2.35 (s, 3H), 2.45 (s, 3H), 4.30 (s, 2H), 4.45 (q, 2H), 4.80 (s, 2H), 6.75 (d, 1H), 7.30 (dd, 1H), 7.40 (d, 1H), 7.75 (d, 2H), 7.95 (d, 2H).

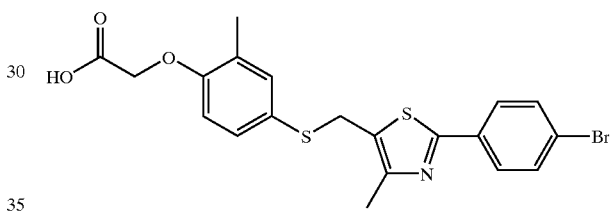

Example 69
2-{2-methyl-4-[({4-methyl-2-[4-bromophenyl]-1,3-thiazol-5-yl}methyl)sulfanyl]phenoxy}acetic acid Example 68 was hydrolyzed as described in general procedure 3. The crude material was chromatographed $CH_2Cl_2$/MeOH (85:15) to afford the title compound (59%) as white solid: mp >250° C.

MS m/z 465 (M+1)

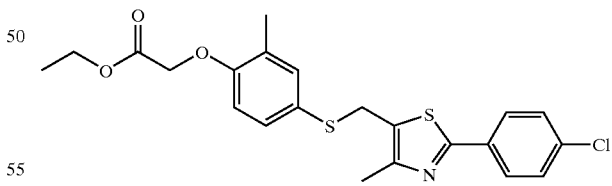

Example 70
ethyl 2-{2-methyl-4-[({4-methyl-2-[4-chlorophenyl]-1,3-thiazol-5-yl}methyl)sulfanyl]phenoxy}acetate Intermediate 48 and intermediate 54 were coupled as described for example 67.-The crude material was chromatographed petroleum ether/EtOAc (90:10) to afford the title compound (53%) as clear oil that solidified upon standing.

1H-NMR (CDCl3) δ1.15 (t, 3H), 2.00 (s, 3H), 2.10 (s, 3H), 3.90 (s, 2H), 4.05 (q, 2H), 4.45 (s, 2H), 6.45 (d, 1H), 6.95 (dd,1 H), 7.00 (d, 1 H), 7.20 (d, 2H), 7.65 (d, 2H).

MS m/z 447

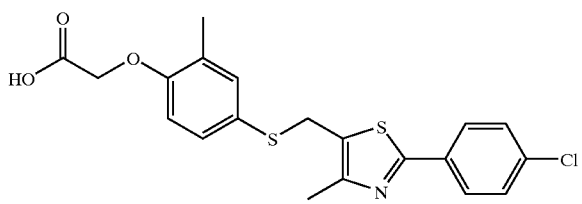

Example 71

2-{2-methyl-4-[({4-methyl-2-[4-chloraphenyl]-1,3-thiazol-5-yl}methyl)sulfanyl]phenoxy}acetic acid Example 70 was hydrolyzed as described in general procedure 3. The crude material was crystallized from acetonotrile to afford the title compound (73%) as a pale yellow solid: mp 109° C.

MS m/z 420

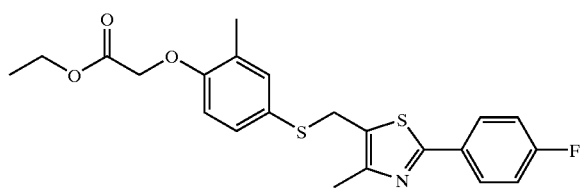

Example 72 ethyl 2-{2-methyl-4-[({4-methyl-2-[4-fluorophenyl]-1,3-thiazol-5-yl}methyl)sulfanyl]phenoxy}acetate Intermediate 49 and intermediate 54 were coupled as described for example 67. The crude material was chromatographed CH$_2$Cl$_2$ (100%) to afford the title compound (72%) as a clear oil that solidified on standing.

1H-NMR (CDCl3) δ1.45 (t, 3H), 2.35 (s, 3H), 2.45 (s, 3H), 4.25 (s, 2H), 4.35 (q, 2H), 4.80 (s, 2H), 6.75 (d, 1H), 7.30 (m, 3H), 7.40 (d, 1H), 8.05 (m, 2H),

MS m/z 431

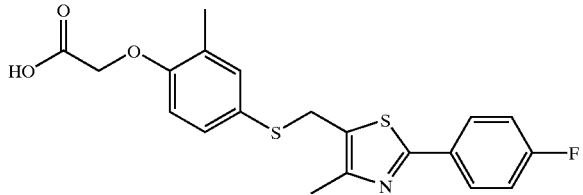

Example 73

2-{2-methyl-4-[({4-methyl-2-[4-fluorophenyl]-1,3-thiazol-5-yl}methyl)sulfanyl]phenoxy}aetic acid Example 72 was hydrolyzed as described in general procedure 3 to afford the title compound (73%) as yellow foam: mp 45–46° C.

Anal. Calcd. for C$_{20}$H$_{18}$FNO$_3$S$_2$: C, 59.53; H, 4.50; N, 3.47; S, 15.89. Found: C, 59.67; H, 5.11; N, 3.38; S, 15.96.

MS m/z 404 (M+1)

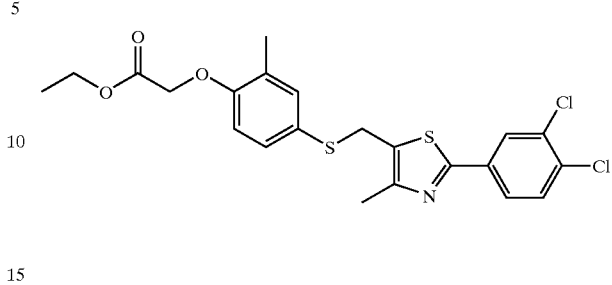

Example 74 ethyl 2-{2-methyl-4-[({4-methyl-2-[3,4-dichlorophenyl]-1,3-thiazol-5-yl}methyl)sulfanyl]phenoxy}acetate Intermediate 50 and intermediate 54 were coupled as described for example 67. The crude material was chromatographed CH$_2$Cl$_2$ (100%) to afford the title compound (49%) as a clear oil that solidified on standing.

1H-NMR (CDCl3) δ1.25 (t, 3H), 2.10 (s, 3H), 2.20 (s, 3H), 4.05 (s, 2H), 4.15 (q, 2H), 4.55 (s, 2H), 6.50 (d, 1H), 7.05 (dd, 1H), 7.15 (d, 1H), 7.40 (d, 1H), 7.60 (dd, 1H), 7.90 (d, 1H).

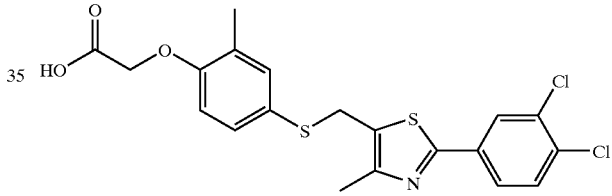

Example 75

2-{2-methyl-4-[({4-methyl-2-[3,4-dichlorophenyl]-1,3-thiazol-5-yl}methyl)sulfanyl]phenoxy}acetic acid Example 74 was hydrolyzed as described in general procedure 3. The crude material was precipitated from ether to afford the title compound (75%) as a white solid: mp 143° C.

Anal. Calcd. for C$_{20}$H$_{17}$Cl$_2$NO$_3$S$_2$.0.2H$_2$O : C, 52.03; H, 3.75; N, 3.03; S, 13.89. Found: C, 52.00; H, 3.321; N, 2.96; S, 12.76.

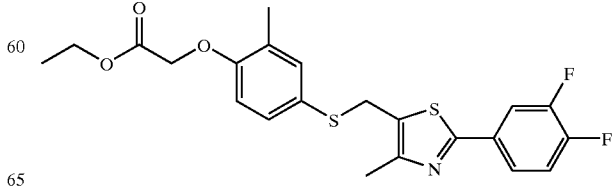

Example 76
ethyl 2-{2-methyl-4-[({4-methyl-2-[3,4-difluorophenyl]-1,3-thiazol-5-yl}methyl)sulfanyl]phenoxy}acetate Intermediate 51 and intermediate 54 were coupled as described for example 67. The crude material was chromatographed heptane/EtOAc (8/2) to afford the title compound (79%) as a yellow solid.

1H-NMR (CDCl3) δ1.05 (t, 3H), 1.95 (s, 3H), 2.05 (s, 3H), 3.85 (s, 2H), 4.05 (q, 2H), 4.40 (s, 2H), 6.40 (d, 1H), 6.85–7.05 (m, 3H), 7.35 (m, 1H), 7.55 (m, 1H).
MS m/z 449

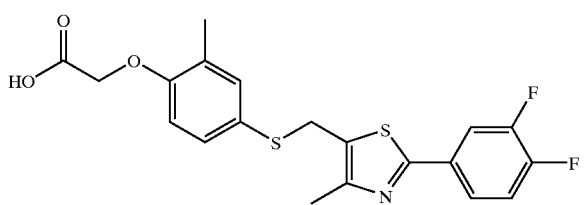

Example 77
2-{2-methyl-4-[({4-methyl-2-[3,4-difluorophenyl]-1,3-thiazol-5-yl}methyl)sulfanyl]phenoxy}acetic acid Example 76 was hydrolyzed as described in general procedure 3. The crude material was crystallized from acetonitrile to afford the title compound (77%) as yellow solid: mp 119° C.
MS m/z 422 (M+1)

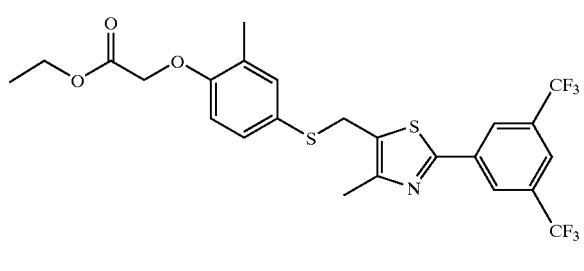

Example 78
ethyl 2-{2-methyl-4-[({4-methyl-2-[3,5-bis(trifluoromethyl)phenyl]-1,3-thiazol-5-yl}methyl)sulfanyl]phenoxy}acetate Intermediate 52 and intermediate 54 were coupled as described for example 67. The crude material was chromatographed cyclohexane/EtOAc (8/2) to afford the title compound (70%) as a clear oil that solidified on standing.

1H-NMR (CDCl3) δ1.20 (t, 3H), 2.15 (s, 3H), 2.20 (s, 3H), 4.05 (s, 2H), 4.15 (q, 2H), 4.55 (s, 2H), 6.50 (d, 1H), 7.05 (dd, 1H), 7.10 (d, 1H), 7.80 (s, 1H), 8.20 (s, 2H).

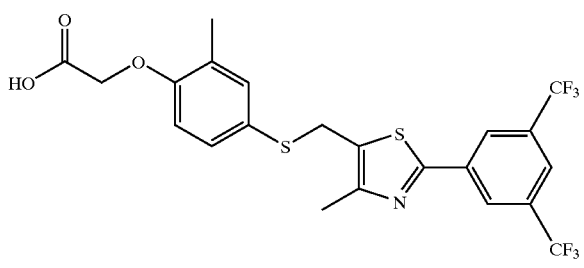

Example 79
2-{2-methyl-4-[({4-methyl-2-[3,5-bis(trifluoromethyl)phenyl]-1,3-thiazol-5-yl}methyl)sulfanyl]phenoxy}acetic acid Example 78 was hydrolyzed as described in general procedure 3. The crude material was precipitated from ether to afford the title compound (89%) as a white solid: mp 178° C.

Anal. Calcd. for $C_{22}H_{17}F_6NO_3S_2$: C, 50.67: H, 3.29; N, 2.69; S, 12.30. Found: C, 50.88; H, 3.68; N, 2.64; S, 10.40.

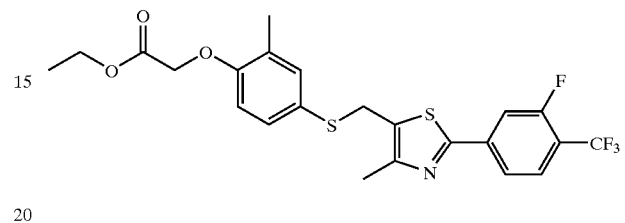

Example 80
ethyl 2-{2-methyl-4-[({4-methyl-2-[3-fluoro-4-(trifluoromethyl)phenyl]-1,3-thiazol-5-yl}methyl)sulfanyl]phenoxy}acetate Intermediate 53 and intermediate 54 were coupled as described for example 67. The crude material was chromatographed $CH_2Cl_2$ (100%) to afford the title compound (50%) as a clear oil that solidified on standing.

1H-NMR (CDCl3) δ1.20 (t, 3H), 2.15 (s, 3H), 2.20 (s, 3H), 4.05 (s, 2H), 4.15 (q, 2H), 4.55 (s, 2H), 6.55 (d, 1H), 7.05 (dd, 1H), 7.15 (d, 1H), 7.55 (t, 1H), 7.65 (m, 2H).
MS m/z 500 (M+1)

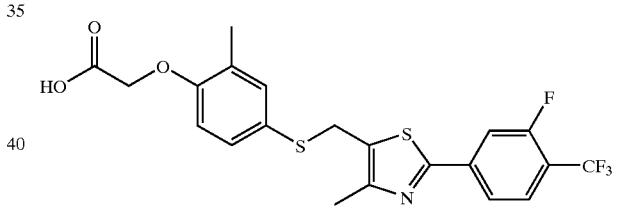

Example 81
2-{2-methyl-4-[({4-methyl-2-[3-fluoro-4-(trifluoromethyl)phenyl]-1,3-thiazol-5-yl}methyl)sulfanyl]phenoxy}acetic acid Example 80 was hydrolyzed as described in general procedure 3. The crude material was precipitated from ether to afford the title compound (81%) as a yellow foam: mp <50° C.

Anal. Calcd. for $C_{21}H_{17}F_4NO_3S_2$: C, 53.50; H, 3.63; N, 2.97; S, 13.60. Found: C53.86; H, 3.63; N, 2.87; S, 13.82.
MS m/z 472 (M+1)

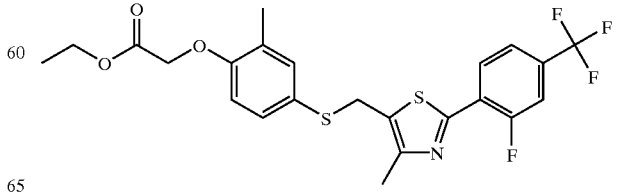

Example 82

Ethyl {4-[({2-[2-fluoro-4-(trifluoromethyl)phenyl]-4-methyl-1,3-thiazol-5-yl}methyl)sulfanyl]-2-methylphenoxy}acetate Intermediate 58 was reacted with Intermediate 25 as described in general procedure 2 to afford the title compound as a yellow oil. (100%)

MS m/z 499 (M+1)

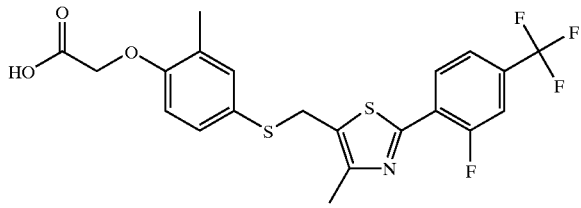

Example 83

{4-[({2-[2-fluoro-4-(trifluoromethyl)phenyl]-4-methyl-1,3-thiazol-5-yl}methyl)sulfanyl]-2-methylphenoxy}acetic acid Example 82 was reacted as described in general procedure 3 to afford the title compound as a white solid (9%)

MS m/z 471 (M+1)

1H NMR (CD3OD) δ=2.19 (s,CH3), 2.22 (s,CH3), 4.24 (s,CH2), 4.70 (s,CH2), 6.75 (d,1Harom) 7.21 (m,2Harom), 7.65 (m,2Harom), 8.35 (t,1Harom)

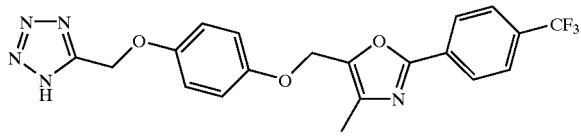

Example 84

5-[4-({4-methyl-2-[4-(trifluoromethyl)phenyl]-1,3-oxazol-5-yl}methoxy)phenoxymethyl]-2H-tetrazole Intermediate 62 was reacted with dibutyltin oxide and trimethylsilyl azide as described in the general procedure to afford the title compound (40.6%) as a white solid: mp 156° C.

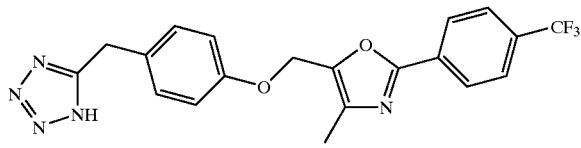

Example 85

5-[4-({4-methyl-2-[4-(trifluoromethyl)phenyl]-1,3-oxazol-5-yl}methoxy)benzyl]-2H-tetrazole Intermediate 63 was reacted with dibutyltin oxide and trimethylsilyl azide as described in the general procedure to afford the title compound (73%) as a white solid: mp 208° C.

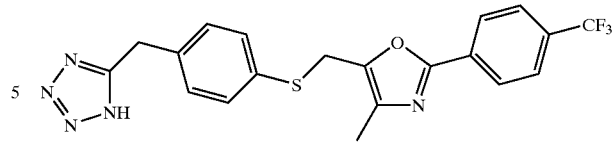

Example 86

5-[4-({4-methyl-2-[4-(trifluoromethyl)phenyl]-1,3oxazol-5-yl}sulfanyl)benzyl]-2H-tetrazole Intermediate 61 was reacted with dibutyltin oxide and trimethylsilyl azide as described in general procedure #7 to afford the title compound (87%) as a white solid: mp 214° C.

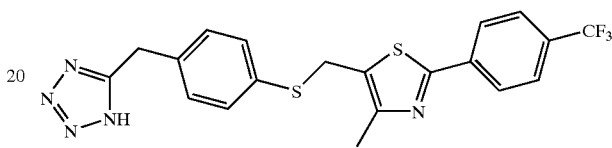

Example 87

5-[4-({4-methyl-2-[4-(trifluoromethyl)phenyl]-1,3-thiazol-5-yl}sulfanyl)benzyl]-2H-tetrazole Intermediate 64 was reacted with dibutyltin oxide and trimethylsilyl azide as described in general procedure #7 to afford the title compound (80%) as a white solid: mp 177° C.

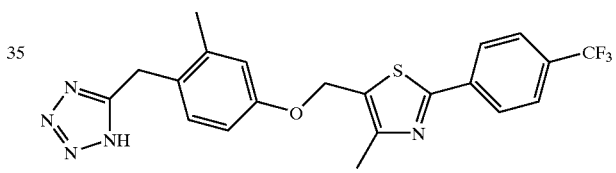

Example 88

5-[2-methyl-4-({4-methyl-2-[4-(trifluoromethyl)phenyl]-1,3-thiazol-5-yl}methoxy)benzyl]-2H-tetrazole Intermediate 65 was reacted with dibutyltin oxide and trimethylsilyl azide as described in general procedure #7 to afford the title compound (44%) as a white solid: mp 165° C.

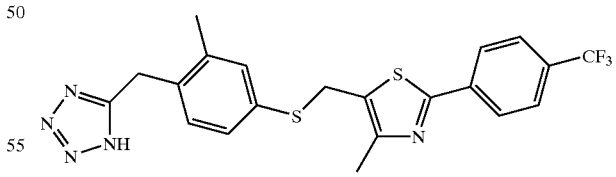

Example 89

5-[2-methyl-4-({4-methyl-2-[4-(trifluoromethyl)phenyl]-1,3-thiazol-5-yl}sulfanyl)benzyl]-2H-tetrazole Intermediate 62 was reacted with dibutyltin oxide and trimethylsilyl azide as described in general procedure #7 to afford the title compound (5%) as a white solid: mp 248° C.

Binding Assay:

Compounds were tested for their ability to bind to hPPARγ hPPARα, or PPARδ using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPARγ, 2-(4-(2-(2,3-Ditritio-1-heptyl-3-(2,4-difluorophenyl)ureido)ethyl)phenoxy)-2-methylbutanoic acid (described in WO/008002) for hPPARα and GW 2433 (see Brown, P. J et al. *Chem. Biol.* 1997, 4, 909–918. For the structure and synthesis of this ligand) for PPARδ) and variable concentrations of test compound, and after equilibration the radioactivity bound to the beads was measured by a scintillation counter. The amount of nonspecific binding, as assessed by control wells containing 50 μM of the corresponding unlabelled ligand, was subtracted from each data point. For each compound tested, plots of ligand concentration vs. CPM of radioligand bound were constructed and apparent $K_i$ values were estimated from non-linear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. *Anal. Biochem.* 1998, 257, 112–119).

Apparent $pK_i$ values were >6.5 for all of the acid Examples described above ($pK_i$=-log of the concentration of test compound required to achieve an apparent $K_i$ value according to the equation $K_i=IC_{50}/1+[L]/K_d$, where $IC_{50}=$ the concentration of test compound required to inhibit 50% of the specific binding of the radioligand, [L] is the concentration of the radioligand used, and $K_d$ is the dissociation constant for the radioligand at the receptor). The ester precursors of the carboxylic acids (e.g. Example 61) had pKi's of less than 6.5 but frequently these esters were active in the transient transfection assay described below, presumably because they hydrolyzed to active acids under the assay conditions.

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehrmann, J. M.; Moore, L. B.; Simth-Oliver, T. A.; Wilkison, W. O.; Willson, T. M.; Kliewer, S. A., An antidiabetic thiazolidinedione is a high affinity ligand for peroxisome proliferator-activated receptor γ (PPARγ), *J. Biol. Chem.*, 1995, 270, 12953-6. The ligand binding domains for murine and human PPARα, PPARγ, and PPARδ were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPARγ assay. The positive control in the hPPARα and hPPARδ assays was 2-[4-(2-(3-(4-fluorophenyl)-1-heptylureido)ethyl)-phenoxy]-2-methylpropionic acid, which can be prepared as described in Brown, Peter J., et. al. *Synthesis Issue* 7, 778–782 (1997), or patent publication WO 9736579.

All of the above acid Examples showed at least 50% activation hPPARδ relative to the positive control at concentrations of $10^{-7}$ M or less. Most of the above acid Examples were at least 10-fold selective for hPPARδ over hPPARα and hPPARγ.

In Vivo Evaluations:

In vivo experiments were performed in db/db mice approximately 60 days old. Animals were randomized into vehicle or compound (n/group) with administration by oral gavage for 7 days, at a volume of 5 ml/kg, b.i.d. After 7 days of treatment animals were anesthetized with isofluorane gas and bled by cardiac puncture for analysis of serum glucose, triglyceride, total and HDL cholesterol, and non-esterified free fatty acid concentrations.

The compound of Example 66 was examined in a Rhesus model. A 6-month dose escalation study in obese rhesus monkeys raised HDLc with each dose (0.1, 0.3, 1, and 3 mg/kg bid for 28 days). HDLc increased by more than 40% in each monkey at the 3 mg/kg dose. NMR analysis of lipoprotein particle composition showed a shift in the LDLc composition to fewer and larger LDLc particles. Serum TG concentrations decreased by more than 30% in each monkey. Fasting insulin decreased by more than 20% in each monkey. Serum fibrinogen concentrations decreased by 10–20%, with peak activity observed at doses of 0.3 and 1 mg/kg.

What is claimed is:

1. A method for lowering triglycerides in a subject comprising the administration of a therapeutic amount of a hPPAR delta agonist of Formula (I)

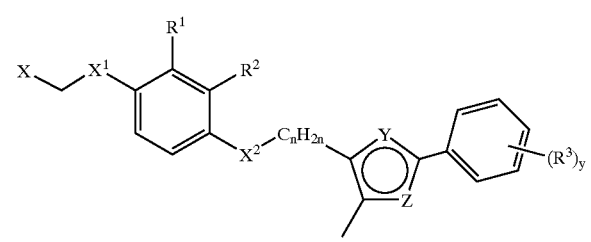

wherein

X represents a COOH (or a hydrolysable ester thereof);

$X^1$ is O or S;

$X^2$ represents O or S;

$R^1$ and $R^2$ independently represent H, $CH_3$, $OCH_3$, or halogen, n is 1 or 2, one of Y and Z is N and the other is S or O;

y represents 1 or 2;

each $R^3$ independently represents $CF_3$ or halogen.

* * * * *